US012596116B2

(12) United States Patent (10) Patent No.: US 12,596,116 B2
Kjaer et al. (45) Date of Patent: Apr. 7, 2026

(54) SENSOR ASSEMBLY AND POROUS MEMBRANE SENSOR ELEMENT

(71) Applicant: RADIOMETER MEDICAL APS, Brønshøj (DK)

(72) Inventors: Thomas Kjaer, Brønshøj (DK); Nicolai Brejnholt, Brønshøj (DK); Willy Lindegaard Andersen, Brønshøj (DK); Henrik Siiger, Brønshøj (DK)

(73) Assignee: RADIOMETER MEDICAL ApS, Brønshøj (DK)

( * ) Notice: Subject to any disclaimer, the term of this patent is extended or adjusted under 35 U.S.C. 154(b) by 929 days.

(21) Appl. No.: 17/780,599

(22) PCT Filed: Dec. 21, 2020

(86) PCT No.: PCT/EP2020/087497
§ 371 (c)(1),
(2) Date: May 27, 2022

(87) PCT Pub. No.: WO2021/123441
PCT Pub. Date: Jun. 24, 2021

(65) Prior Publication Data
US 2024/0027423 A1 Jan. 25, 2024

(30) Foreign Application Priority Data
Dec. 19, 2019 (DK) .............................. PA201901513

(51) Int. Cl.
*G01N 33/49* (2006.01)
(52) U.S. Cl.
CPC ....... *G01N 33/491* (2013.01); *G01N 33/4915* (2013.01)
(58) Field of Classification Search
CPC .. A61B 5/14546; A61B 5/1455; G01N 33/49; G01N 2021/4709; G01N 2021/4742;
(Continued)

(56) References Cited

FOREIGN PATENT DOCUMENTS

| CN | 1997885 A | 7/2007 |
|----|-----------|--------|
| CN | 101278186 A | 10/2008 |

(Continued)

OTHER PUBLICATIONS

Archibong et al., Optofluidic spectroscopy integrated on optical fiber platform, Sensing and Bio-Sensing Research, vol. 3, 2015, pp. 1-6, ISSN 2214-1804, https://doi.org/10.1016/j.sbsr.2014.11.002. (Year: 2015).*

(Continued)

*Primary Examiner* — Dean Kwak
(74) *Attorney, Agent, or Firm* — FBT Gibbons LLP

(57) ABSTRACT
The present invention relates a porous membrane sensor element for the detection of an analyte in a complex fluid sample. The porous membrane sensor element comprises: a porous membrane sensor housing penetrated by a flow channel defining an axial direction, the flow channel comprising a sample space; a porous membrane with a front side defining a sensor surface for contacting the fluid sample, the sensor surface facing towards the sample space, the porous membrane comprising pores extending from respective openings at the sensor surface into the porous membrane, wherein the pores are configured with regard to the analyte for diffusive fluid communication with the sample space; and an optical subassembly comprising a light guide core, the light guide core comprising an input branch, an output branch, and a coupling interface arranged to contact a backside of the porous membrane opposite to the front side and facing away from the sample space; wherein the input and output branches are directed towards the coupling interface. The input branch and the output branch are arranged in a common light guide plane arranged perpendicular to the sensor surface. According to a further aspect, a sensor assembly comprises a porous membrane sensor element integrated within a sample chamber thereof.

17 Claims, 6 Drawing Sheets

(58) Field of Classification Search
CPC ..... G01N 2021/773; G01N 2021/7763; G01N 21/31; G01N 21/474; G01N 21/78; G01N 33/491; G01N 33/4915; G01N 15/01; G01N 15/1434; G01N 21/62; G01N 21/7703

See application file for complete search history.

(56) References Cited

FOREIGN PATENT DOCUMENTS

| CN | 107091824 A | 8/2017 | |
| CN | 107430071 A | 12/2017 | |
| CN | 108463711 A | 8/2018 | |
| JP | 2008-505324 A | 2/2008 | |
| WO | WO 2006/014410 A1 | 2/2006 | |
| WO | WO 2017/085162 A1 | 5/2017 | |
| WO | WO2017085180 A1 | 5/2017 | |
| WO | WO-2018210784 A1 * | 11/2018 | ......... A61B 5/14546 |
| WO | WO 2019/197308 A1 | 10/2019 | |

OTHER PUBLICATIONS

Archibong, Edikan et al., "Optofluidic spectroscopy integrated on optical fiber platform," *Sensing and Bio-Sensing Research*, vol. 3, pp. 1-6 (2015).

Yang, L. et al., "Sol-Gel-Based, Planar Waveguide Sensor to Gaseous Iodine," *Analytical Chemistry*, vol. 68, No. 11, pp. 1834-1841 (1996).

International Search Report of International Application No. PCT/EP2020/087497, dated Mar. 15, 2021.

Written Opinion of the International Search Authority for International Application No. PCT/EP2020/087497 (six pages).

Chinese Office Action for CN 202080088233.5, mailed Dec. 10, 2024, 10 pages.

Japanese Office Action for JP 2022-538309, mailed Jun. 30, 2023, 4 pages.

* cited by examiner

1

SENSOR ASSEMBLY AND POROUS MEMBRANE SENSOR ELEMENT

This application is a national stage filing under 35 U.S.C. § 371 of International Application No. PCT/EP2020/087497, filed on Dec. 21, 2020, which claims priority to Danish Patent Application No. PA201901513, filed on Dec. 19, 2019. The contents of these applications are each incorporated herein by reference.

The present invention relates to a porous membrane sensor element for the detection of an analyte in a complex fluid sample. According to a further aspect, the invention relates to a sensor assembly comprising such a porous membrane sensor element integrated within a sample chamber thereof. According to a particular aspect, the invention relates to a re-usable porous membrane sensor element, and a re-usable sensor assembly comprising such a re-usable porous membrane sensor element. According to a further aspect the re-usable porous membrane sensor element is adapted for use in a multiple parameter analyzer instrument, such as an analyzer instrument for analyzing multiple parameters in body fluid samples. According to a yet further aspect the re-usable sensor assembly comprising such a re-usable porous membrane sensor element is adapted for use in a multiple parameter analyzer instrument, such as an analyzer instrument for analyzing multiple parameters in body fluid samples.

BACKGROUND OF THE INVENTION

Detecting an analyte in a complex fluid containing continuous and discontinuous fractions is a challenging, but frequently encountered measurement problem. Typically the measurements involve steps of sample preparation including separation, e.g. by filtration, sedimentation and/or centrifugation, and subsequent detection measurement steps using chemical indication reactions and/or physical interactions sensitive to the analyte in question. An intricate challenge in this context is often the preparation and presentation of a proper sample for the detection without compromising the measurement, in particular if a volume of the available sample is small, and if the fluid to be analyzed is very complex. On top of that, very often in such a situation, multiple parameters are to be determined on the same sample, which imposes additional constraints of integrating a given measurement for the detection of an analyte with measurements of other parameters.

Therefore, there is a need for a highly sensitive, yet simple and fast technique allowing for the selective detection of an analyte in a complex fluid, which is furthermore adapted for easy integration with other measurement techniques for determining multiple parameters of the same sample. The desired technique is furthermore required to provide for gentle separation, extraction, and/or isolation of the analyte for the detection measurements, i.e. without compromising the remaining fractions of the fluid to be analyzed.

Such a detection technique is relevant for various industries, ranging from food industry, over wastewater treatment, to pharmaceutical applications and medical devices, where known techniques often require large sample volumes and time-consuming analysis procedures.

One example for the application of such a measurement technique is in relation to the detection of an analyte in body fluids, such as a patient's blood sample. The analyte can be any of a laboratory's test parameters for body fluid analysis, which is detectable by light, e.g. spectrophotometry. As one source of interference in the analysis of blood, hemolysis may affect the measurement of a number of blood parameters as determined in blood parameter analyzers. Disregarding a level of free hemoglobin in the blood sample may thus mislead an unaware person and as a result provide a wrong diagnosis based on the affected blood parameter value. However, reliably determining a level of free hemoglobin present in the plasma fraction of a whole blood sample hitherto involved a complex process requiring separation of the plasma fraction from the cellular components and a subsequent analysis of the separated plasma fraction. Such a procedure is time consuming and may be prohibitive in cases where only very small samples are available at a time, such as in neonatal care with a continued monitoring of blood parameters in the infant. Other approaches for measuring components present in the plasma fraction in whole blood involve the separation of a plasma fraction from cellular components by microfiltration techniques in e.g. a microfluidic device, prior to analysis of the plasma fraction in a dedicated measurement in the microfluidic device. For example, a recent scientific article by Archibong et al. and published in Sensing and Bio-Sensing Research 3 (2015), p.1-6, discloses a miniature measuring chamber for optically analyzing a plasma fraction that has been separated from a whole blood sample. In this type of device, a miniature microfluidic chamber is attached to the interface of an optical fiber. The bottom of the microfluidic chamber consists of a porous membrane that allows fluids and chemical compounds to flow inside the device, while at the same time filtering out undesired particles. The inside of the microfluidic chamber receiving the filtrate can be optically probed through a single optical fiber in normal-incidence reflection geometry. However, due to clogging issues, the disclosed device is most useful as a disposable rather than for continued and repetitive use, since a complete washout of a sample after measurement may be difficult or at least very time-consuming and unreliable, at the further risk of cross-contamination between subsequent samples. Furthermore, in this particular type of device, additional challenges for obtaining quantitative results from the optical probing may arise, due to pressure-induced deformation of the filtration membrane resulting in a change of the optical path for probing the filtrate.

In a further example, namely applications in food industries, such as dairy industry, most traditional methods of filtering and detecting comprise filter paper, sieves and the like for visual inspection, spectrometry or bacterial counting of the residues with the above-mentioned disadvantages of requiring relatively large sample volumes and involving time-consuming measuring procedures that are detrimental to the sample, and that are incompatible with integrated multiple-parameter measurements to be performed on the same sample. Similar challenges are also encountered in the field of environmental technologies, such as wastewater analysis and treatment, where most traditional methods of filtering and detecting comprise filter papers, sieves and the like for spectrometry and bacterial counting of the residues.

Filtration-based approaches have several disadvantages when used for analyzing e.g. whole blood samples. Filtration devices inherently rely on a fluid flow of at least the filtrate through the pores of the filter from a sample feed to a filtrate analysis/measurement chamber. In through-flow geometries, the retentate (here the red blood cells) gradually clogs the filtration pores. In crossflow geometries, the retentate is lead along the surface of the filtering membrane, thereby reducing but not removing the problem with clogging, especially if the system is intended for repetitive use (more than 10-100 samples). Crossflow geometry also induces friction and shear interaction between the retentate and the surface of the filtering device.

An improved separation and measurement technique addressing these issues is disclosed in the co-pending international patent applications by the applicant, WO 2017/085162 A1, WO 2017/085180 A1, and WO 2019/197308 A1, which are hereby incorporated by reference.

Again, a particularly challenging field of application is the analysis of body fluids in a point-of-care set-up. Modern point-of-care analyzers for analyzing multiple parameters in body fluid samples, such as for the analysis of arterial or venous blood, are subject to severe requirements and constraints of patient safety, user friendliness, short measurement times in the range of a minute or below, reliability/reproducibility, precision of the quantitative output, as well as compliance with quality management systems and safety directives for medical measurement apparatus to only name a few. The precise and compliant results have to be obtained on very small amounts of sample fluid (typically less than 100 µl, or even less than 50 µl) in agreement with the above-mentioned requirements and constraints. Most advanced point-of-care analyzer systems are therefore designed around an automated fluid handling and measurement infrastructure with a compact sensor assembly at its core. Such sensor assemblies are for repetitive use and typically have a sample space defined by sample chamber walls with miniaturized high precision sensors directly integrated in at least one of the walls. An example of such a sensor assembly for body fluids is e.g. disclosed in the European patent specification EP 2 147 307 1. The sensor assembly of EP 2 147 307 1 comprises electrochemical and optical sensor elements, which is particularly suitable for simultaneously measuring a plurality of different parameters in body fluid samples, such as blood parameters. It is therefore desirable that a new measurement technique fulfilling the above-stated needs for highly sensitive, simple and selective detection of an analyte in a complex fluid should be suited for integration with such a sensor assembly having a sample channel width in the millimeter range and a sample channel height in the sub-millimeter range.

A device for detecting an analyte in a fluid sample by optical probing is described in the above-mentioned application WO 2019/197308 A1 by the applicant, wherein a porous sensor element is arranged in a chamber wall of a sample chamber comprising for holding the fluid sample. The sensor surface has open pores and faces towards the sample chamber to contact the fluid sample, and to receive in the pores analytes from at least the continuous fraction of a complex fluid sample by means of diffusion.

However, there still is a need for an improved device and method for the detection of an analyte in a fluid with a fast and reliable response, which can be implemented in a miniaturized manner. Further, there is a particular need for providing a porous membrane sensor element, which is adapted for optical probing, and which would facilitate close integration within a sensor assembly and device for the analysis of a fluid sample, such as within an automated point-of-care analyzer system for body fluids. More generally, there still is a need for an improved device and method for the detection of substances in a fraction of a complex fluid, such as a whole blood sample with a fast and reliable response, which is adapted for miniaturization and integration in a fluid analyzer system, in particular an analyzer system for multiple-parameter measurements on the same fluid sample.

According to one aspect, an object of the present invention is therefore to provide an improved detection device and/or method overcoming at least some of the disadvantages of known devices, sensors, systems and/or methods for specific detection of analytes in the continuous fraction of a complex fluid, such as for detecting an analyte in a plasma fraction of a whole blood sample. According to a further aspect, an object of the present invention is to provide such a detection device, which can be miniaturized for integration within a sensor assembly.

SUMMARY OF THE INVENTION

According to one aspect, the object is achieved by a porous membrane sensor element according to claim 1, with advantageous embodiments as defined in the dependent claims referring to it, and as further disclosed in the present application. According to a further aspect, the object is also achieved by a sensor assembly comprising such a porous membrane sensor element. In one or more aspects, the object is further achieved by a re-usable porous membrane sensor element, and a re-usable sensor assembly comprising such a re-usable porous membrane sensor element as disclosed herein, which according one or more aspects are adapted for use in a multiple parameter analyzer instrument, such as an analyzer instrument for analyzing multiple parameters in body fluid samples. Moreover, each aspect is not necessarily to be construed as an individual aspect, i.e. different aspects may readily be combinable.

In the context of point-of-care measurement systems (in the art also referred to as 'bedsite' systems) and laboratory environments alike, blood gas analysis is oftentimes undertaken by users, such as nurses, who may not be users trained in use of blood gas analyzers. In particular, users' correct placement of a handheld blood sample container, such as a syringe or a capillary tube, at an inlet structure of the blood gas analysis has been found to constitute a challenging aspect in aspiration of the blood sample into the blood gas analyzers. Incorrect positioning or alignment of the blood sample container relative to the inlet structure may not only lead to disturbing delays and/or frustrations in users' daily workflows but may even in result in loss of blood samples or contamination of the blood gas analyzer or its surroundings.

According to a specific aspect of the invention, there is presented use of a system/method according to any of the embodiments herein, for point-of-care (POC) measurement on analyte parameters in body fluids, and in particular in a whole blood sample.

POC measurement is also referred to as 'bed site' measurement in the art. In the present context, the term 'point-of-care measurement' should be understood to mean measurements which are carried out in close proximity to a patient, i.e. measurements that are not carried out in a laboratory. Thus, according to this embodiment, the user of the blood gas analyzer performs measurement of a whole blood sample in a handheld blood sample container in the proximity of the patient, from whom the blood sample is taken, e.g. in the hospital room or ward accommodating the patient's bed, or in a nearby room of the same hospital department. In such use, the level of expertise of the user oftentimes varies from novice to experienced, and the capability of the blood gas analyzer to automatically output instructions matching each individual user's skills on the basis of sensor input is thus particularly beneficial in such environments.

According to one aspect, the invention relates to a porous membrane sensor element for the detection of an analyte in a complex fluid sample, the porous membrane sensor element comprising: a porous membrane sensor housing penetrated by a flow channel defining an axial direction, the flow channel comprising a sample space; a porous membrane with a front side defining a sensor surface for contacting the fluid sample, the sensor surface facing towards the sample space, the porous membrane comprising pores extending from respective openings at the sensor surface into the porous membrane, wherein the pores are configured with regard to the analyte for diffusive fluid communication with the sample space; and an optical subassembly comprising a light guide core, the light guide core comprising an input branch, an output branch, and a coupling interface arranged to contact a backside of the porous membrane opposite to the front side and facing away from the sample space; wherein the input and output branches are directed towards the coupling interface; wherein the input branch and the output branch are arranged in a common light guide plane arranged perpendicular to the sensor surface.

The porous membrane sensor element is useful for analyzing complex fluids comprising a continuous fraction and a discontinuous fraction, in particular for selectively detecting an analyte in the continuous fraction of the complex fluid. The porous membrane sensor element is particularly useful for miniaturization and/or integration in a sensor assembly, as further detailed below, in particular for use in a fluid analyzer set-up for measuring multiple analyte parameters, e.g. in a modern blood analyzer.

In some embodiments, the sample space is formed in a flow channel, between an inlet and an outlet. Furthermore, the porous membrane is arranged in a wall of the sample space with the pore openings on the sensor surface facing towards the sample space. The sample space may thus be arranged such that a fluid sample of a complex fluid introduced from the inlet is presented at the sensor surface of the porous membrane facing towards the sample space. At least a fraction of the complex fluid is in diffusive communication with the pores, such as dead-end pores, of the porous membrane for introducing a representative subsample into the pores as further detailed below. The optical subassembly coupled to the back side of the porous membrane then enables performing selective optical measurements on the subsample in the pores from the back side of the porous membrane as also discussed elsewhere herein. After the measurement is performed, the fluid sample can be removed from the sample space to the outlet, and rinsed with a rinsing fluid. Rinsing the sample space also rinses the pores for analytes through diffusive transport with rinsing fluid in the sample space. The porous membrane sensor element can then be re-used for a new measurement on a further fluid sample different from the previous fluid sample.

In some embodiments, the porous membrane with dead-end pores is arranged in diffusive communication with the sample space formed in a flow channel extending from an inlet to an outlet. Thereby, a re-usable device is provided allowing for measuring on a plurality of fluid samples in respective measurement cycles. Typically, each measurement cycle comprises: presenting a fluid sample in the sample space; performing measurements on a sub-sample of the fluid sample in diffusive communication with the pores of the porous membrane as also further detailed elsewhere herein; removing the sample from the sample space; and rinsing the sample space with a rinsing fluid. This configuration of the porous membrane in diffusive communication with a sample space formed in a flow channel thereby allows for integrating the optical measurement in a re-usable sample assembly adapted for use in an analyzer for measuring multiple parameters.

The analyte is extracted from the fluid sample into the porous membrane by means of diffusion. The analyte may then be detected by optical probing using the optical The term "detection" as used herein is considered to include the mere qualitative detection of the presence of a given analyte and/or a quantitative measurement, such as a measurement for determining the concentration of the analyte in the complex fluid sample. The pores of the porous membrane are in diffusive fluid communication with the sample chamber. The pores are configured with regard to the analyte for diffusive fluid communication between a fluid in the pores and the fluid sample in the sample space of the porous membrane sensor element. The pores are thus configured for exchanging the analyte with the continuous fraction of the complex fluid sample in the sample chamber through diffusive transport while preventing the much larger particles of the discontinuous phase of the complex fluid sample to enter the pores.

The terms "optical" and "light" and related terms generally refer to electromagnetic radiation in the visible, infrared, and ultraviolet spectral ranges: the term "visible" typically refers to electromagnetic radiation with wavelengths in the range of 400 nm-700 nm; the term "infrared" broadly refers to electromagnetic radiation with wavelengths in the range of 700 nm-1 mm, with typical subranges of about 700 nm-3 μm in the "near-infrared", 3 μm-50 μm in the "mid-infrared", and 50 μm-1 mm in the "far-infrared"; the term "ultraviolet" or "UV" broadly refers to electromagnetic radiation with wavelengths in the range of 10 nm-400 nm, with typical subranges of 300 nm-400 nm in the "near ultraviolet", 200 nm-300 nm in the "middle ultraviolet", and 122 nm-200 nm in the "far ultraviolet". The skilled person will understand that the usefulness of the mentioned spectral ranges for a given sensor element, and in particular for a given translucent membrane material, will depend on the compatibility of spectral ranges and materials for propagating input and output light through these materials.

The porous membrane is a translucent membrane. The term "translucent" refers to a material's property of allowing light to pass through. The term "transparent" refers to the property of a material of allowing light to pass through the material without being scattered. The term "transparent" is thus considered a sub-set to the term "translucent". The backside of the translucent membrane is typically parallel to the front side; an additional transparent backing may be applied to the backside in order to provide a mechanical support for stiffening/reinforcing the translucent membrane from the backside. The backing may be, or at least include, a transparent padding filling voids between the translucent membrane and further optical components of the sensor element, such as the input port, and/or the output port. Any void between the backside of the translucent membrane and any of the further optical components may be filled out with a transparent padding component.

The input branch forms an optical input port connected to the backside of the translucent membrane, the backside facing away from the front side. The optical input port is adapted for feeding probing light to a probing region of the translucent membrane through the coupling interface at the backside. The output branch forms an optical output port connected to the backside of the translucent membrane. The optical output port is adapted for collecting an optical response from the translucent membrane through coupling interface at the backside. The optical input port is configured for feeding probing light through the backside into the translucent membrane. The optical output port is configured for collecting an optical response to the probing light from the translucent membrane through the backside. By both injecting the probing light and collecting the optical response from the back side of the translucent membrane, a compact design is achieved allowing for the integration of the sensor element in a miniaturized sample assembly with a very small sample chamber, which is designed for analyzing very small amounts of a sample fluid.

The term "fluid" refers to liquids and/or gases including complex fluids comprising a continuous phase and a discontinuous phase, such as a particulate phase. Examples of relevant fluids to be analyzed using embodiments of the present invention include, but are not limited to body fluids, in particular whole blood sample, the plasma fraction of whole blood, spinal cord fluid, urine, pleura, ascites. Further examples of relevant fluids include wastewater, a pre-prepared fluid for any kind of injection, fluids with a constituent possible to detect by spectroscopy, or a gas such as air, a carbon dioxide containing gas, a carbon monoxide containing gas. The term "sample" refers to the part of the fluid that is used or needed in the analysis with the porous membrane of the invention.

The term "complex fluid" as used herein refers to a fluid with a continuous fraction and a discontinuous fraction, such as a liquid fraction and a particulate fraction. Typically, the analyte is a component in the continuous fraction of the complex fluid sample. The fluid to be analyzed thus contains at least a continuous fraction comprising the analyte. The fluid to be analyzed may further contain a discontinuous fraction, i.e. a particulate fraction. The particulate fraction may include, for example, solid particles, debris and other contaminants, biological cells (such as red blood cells) or microorganisms, liquid droplets, gas bubbles, and combinations thereof. The fluid to be analyzed may be a whole blood sample, the plasma fraction of whole blood, spinal cord fluid, urine, pleura, ascites, wastewater, a pre-prepared fluid for any kind of injection, fluids with a constituent possible to detect by optical probing, such as spectroscopy, or a gas such as air, carbon dioxide containing gas, carbon monoxide containing gas.

The term "whole blood" refers to blood composed of blood plasma, and cellular components. The plasma represents about 50%-60% of the volume, and cellular components represent about 40%-50% of the volume. The cellular components are erythrocytes (red blood cells), leucocytes (white blood cells), and thrombocytes (platelets). Preferably, the term "whole blood" refers to whole blood of a human subject, but may also refer to whole blood of an animal. Erythrocytes constitute about 90%-99% of the total number of all blood cells. They are shaped as biconcave discs of about 7 μm in diameter with a thickness of about 2 μm in an un-deformed state. The erythrocytes are highly flexible, which allows them to pass through very narrow capillaries, reducing their diameter down to about 1.5 μm. One core component of erythrocytes is hemoglobin, which binds oxygen for transport to the tissues, then releases oxygen and binds carbon dioxide to be delivered to the lungs as waste product. Hemoglobin is responsible for the red color of the erythrocytes and therefore of the blood in total. Leucocytes make up less than about 1% of the total number of all blood cells. They have a diameter of about 6 μm to about 20 μm. Leucocytes participate in the body's immune system e.g. against bacterial or viral invasion. Thrombocytes are the smallest blood cells with a length of about 2 μm to about 4 μm and a thickness of about 0.9 μm to about 1.3 μm. They are cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50%-60% by volume). Plasma is devoid of cells. It contains all coagulation factors, in particular fibrinogen and comprises about 90%-95% water, by volume. Plasma components include electrolytes, lipid metabolism substances, markers, e.g. for infections or tumors, enzymes, substrates, proteins and further molecular components.

The term "wastewater" refers to water that has been used, as for washing, flushing, or in a manufacturing process, and so contains waste products and/or particles and is thus not suitable for drinking and food preparation.

The analyte may be any substance detectable by a suitable probing technique, such as optical probing, such as further detailed below. For example, the analyte may be a subset of molecules that may be present in the continuous phase of the fluid to be analyzed. For example, when analyzing a whole blood sample, the analyte may be a particular drug, and the measurement may be for determining a drug content in the plasma phase, e.g. to determine drug uptake and adjust dosing of the drug accordingly. In another example of analyzing a whole blood sample, the analyte may be hemoglobin for determining a degree of hemolysis. More generally, the porous membrane sensor element may be configured for detecting a high molecular weight analyte. In the context of the present application, the term "high molecular weight" refers to a molecular weight of 10 000 Da or above, such as 30 000 Da or above, or such as 50 000 Da or above. An example of detecting high molecular weight analytes in a continuous fraction of a complex fluid is detecting hemolysis in a whole blood sample.

As mentioned above, the porous membrane sensor element has a sensor surface for contacting a fluid to be analyzed. The sensor surface is formed at the front side of the translucent membrane and the reflecting layer applied to the front side. The translucent membrane contains small pores, preferably dead end pores, extending from the front side, through the reflective layer into the translucent membrane. Each of the small pores has an opening through which it can communicate with a fluid space at the front side of the translucent membrane. The pores thus penetrate the reflecting layer to allow for fluid communication between the pores and the fluid space. The pores extend from the respective opening at the front side into the translucent membrane in a direction towards the backside. The pores are preferably "dead end" meaning that the pores end within the translucent membrane. The dead end pores do not continue all the way through the translucent membrane to the backside or to any common reservoir or recipient inside the membrane. The pores are only in fluid communication with the fluid space at the front side of the translucent membrane. Note that in some embodiments, the dead end pores can be crisscrossing and at least some of the pores may thus be connected to each other forming an X-shape, a Y-shape, a V-shape, or similar interconnected shapes. Such a configuration is equally considered as dead end, since the pores are only filled from the front side and no significant net mass transport passing through the pores occurs under operation, even if they cross each other.

The translucent membrane may be made from transparent polymer membranes with pores fabricated therein using, for example, so-called track-etching techniques as disclosed in the co-pending international patent applications, WO 2017/085162 A1 and WO 2017/085180 A1, which are hereby incorporated by reference.

The pores form vials/cuvettes for selectively receiving an analyte from a first fraction of the fluid, in particular via diffusion/diffusive transport, whereas a particulate fraction is effectively prevented from entering the pores. These vials/cuvettes are placed at least in a probing region for efficient interaction of probing light with the analyte. The openings of the pores are dimensioned such that a particulate fraction of the fluid to be analyzed is kept outside the pores, while allowing an analyte from a further fraction, e.g. a continuous fraction, to enter through the pores into the translucent membrane, so that the probing light injected from the input port can interact with the analyte and thus detect the analyte by optical probing. By appropriately dimensioning the opening of the pores at the front side it is possible to prevent e.g. red blood cells of a whole blood sample at the sensor surface from entering the pores, while allowing relevant components in the plasma fraction of the whole blood sample to enter the pores, wherein relevant components are substances present in the plasma fraction of the whole blood sample (or more generally in the relevant fraction of the fluid sample) and that are to be measured/detected using the sensor.

By this configuration, it is achieved that a small, but representative analyte fraction is gently extracted from the complex fluid and efficiently exposed to the probing light in the probing region with a high degree of overlap. This separation is achieved in a particularly simple and fast manner, since the probing region is arranged directly at the surface of the translucent membrane with the pores penetrating directly into the translucent membrane, and with a relatively short distance from their respective openings at the sensor surface to the location of probing, thus facilitating a particularly rapid diffusive exchange of the sample.

Typical cross-sectional dimensions of the pores are in the micron and sub-micron range down to about 100 nm. Analyte transport into and out of the pores is achieved by diffusion. For efficient operation, the pores are filled with a priming fluid, which preferably is filled into the pores in a priming step, e.g. prior to performing the first detection measurement. The priming fluid may not affect the fluid to be analyzed. The priming fluid thus has to be compatible with the fluid to be analyzed. Advantageously, the priming fluid may be a rinsing fluid, such as an aqueous buffer solution, which may also be used for rinsing a sample chamber during filling, emptying and re-filling procedures for replacing samples of a fluid to be analyzed. The rinsing fluid may also be a reference fluid or a calibration fluid.

Advantageously according to some embodiments, the pores are filled with a liquid. Priming the pores with a known liquid allows for extracting a subsample representative of the relevant components in the fluid to be analyzed into the pores by diffusion alone. This provides for a fast, efficient and well-controlled exchange of the analyte via the pores into and out of the optical probing region. Advantageously according to some embodiments, the liquid is an aqueous solution. This is particularly useful for the detection of water-soluble analytes. Alternatively, it is conceivable that the pores are filled with a non-aqueous liquid, which e.g. is particularly useful when the fluid to be analyzed is also a non-aqueous liquid.

Under operation, the front side of the translucent membrane may be contacted with e.g. a whole blood sample or a fluid. The small pores in the translucent membrane communicate with the whole blood sample or fluid through the openings in the front side. The pore openings are dimensioned to extract selectively a sub-sample of the plasma phase of the whole blood sample or to extract a sub-sample of the fluid including the analyte. No red blood cells can enter the pores through the openings on the front side of the translucent membrane. Nothing larger than the pore diameter can enter the pores, which excludes e.g. any debris included in the fluid. As mentioned, the pores are preferably dead end, only communicating with the front side of the translucent membrane, i.e. the sub-sample is extracted for optical probing inside the pores and after the measurement discharged again through the same openings in the front side of the translucent membrane. The sub-sample volume corresponds to the total internal volume of the pores. No filtration and net mass transport of any filtrate occurs through the pore-containing layer—neither into any common filtrate recipient nor to any filtrate outlet. The optical detection will then be performed only on the sub-sample contained in the pores. The reflective layer optically separates the optical probing region in the translucent membrane from the fluid space containing the whole blood sample or the fluid. By optically separating the probing region from the fluid space, any contribution of the intact red blood cells of the whole blood sample or of the debris in the fluid to the probed signal can be effectively suppressed. The measurement is thus specific to the content of analyte in the fluid.

The small sub-sample with a representative content of the relevant components may be transferred to the pores in any suitable manner. The small dead end pores allow for a very efficient and fast extraction of the sub-sample for optical probing from a whole blood sample or a fluid through the openings in the front side by means of capillary forces and/or diffusion. In a typical operation mode, the front side surface of the translucent membrane is contacted by a rinsing fluid prior to contacting the front side with a whole blood sample or fluid that is to be analyzed. Thereby, the pores are 'primed' with a prefill of a liquid that is compatible with the whole blood sample or the fluid, and in particular a liquid that is compatible with the plasma phase if the fluid is whole blood, such as an aqueous solution commonly used for rinse, calibration and/or quality control purposes in blood analyzers. Typical rinse liquids used for e.g. wash-out in whole blood analyzer systems may be used as such a liquid. Rinse liquids are aqueous solutions comprising $K^+$, $Na^+$, $Cl^-$, $Ca^{2+}$, $O_2$, pH, $CO_2$, and $HCO^{3-}$ in concentrations corresponding to human plasma. When the whole blood sample or fluid is then brought in contact with the front side surface that is primed with a plasma compatible liquid/fluid compatible liquid, a representative sub-sample of components in the plasma phase of the whole blood sample or of the fluid is extracted and transferred in a very efficient and gentle manner by means of diffusion of the relevant components into the prefilled pore. In particular, any concentration gradient in the content of the analyte between the fluid and the reference liquid in the pores drives a diffusive transfer, thereby producing in the pores a sub-sample with an analyte concentration representative of the analyte concentration in the fluid.

The sub-sample volume corresponds to the total internal volume of the pores. No filtration and net mass transport of any filtrate occurs through the pore-containing layer during measurement—neither into any common filtrate recipient nor to any filtrate outlet. The optical detection is then performed only on the sub-sample contained in the pores. The confinement of the input light to the translucent membrane optically separates optical probing from the fluid space containing the whole blood sample or the fluid. By optically separating the optical probing from the fluid space, contributions of the intact red blood cells of the whole blood sample or of the debris in the fluid to the probed signal can be effectively suppressed. The measurement is thus specific to the content of analyte in the fluid.

The following embodiments disclose advantageous rules and ranges for dimensioning the pores, in particular for use in a sensor element in the context of optically probing body fluids.

Further, according to some embodiments of the sensor element, a cross-sectional dimension of the openings of the pores is about 1 µm or less, about 800 nm or less, preferably about 500 nm or less, or even about 400 nm or less. The cross-sectional dimension of the pore openings is preferably adapted so as to balance size selectivity (smaller pore opening diameter) against a rapid exchange of sub-sample/analyte (larger pore opening diameter)—depending on the application. The given values are, for example, particularly useful for the analysis of body fluids, such as whole blood with an analyte in the plasma fraction.

Further, according to some embodiments of the sensor element, a cross-sectional dimension of the openings of the pores is at least 200 nm. The cross-sectional dimension of the pore openings is preferably adapted so as to balance size selectivity (smaller pore opening diameter) against a rapid exchange of sub-sample/analyte (larger pore opening diameter)—depending on the application. The values of the recited range are, for example, particularly useful for the analysis of body fluids, such as whole blood with an analyte in the plasma fraction.

Further, according to some embodiments of the sensor element, a length of the pores in an axial direction along the pores is less than 100 µm, less than 50 µm, and preferably less than 30 µm. The length of the pores is preferably adapted so as to balance a desire to provide an increased sample volume (longer pore length) for interaction with the optical probing field in the probing region against rapid exchange of sample/analyte (shorter pore length)—depending on the application. The given values are particularly useful for the analysis of body fluids, such as whole blood with an analyte in the plasma fraction of the whole blood sample.

Further, according to some embodiments of the sensor element, a length of the pores in an axial direction along the pores is at least 1 µm, at least 2 µm, at least 5 µm, and preferably at least 10 µm. The length of the pores is preferably adapted so as to balance a desire to provide an increased sample volume (longer pore length) for interaction with the optical probing field in the probing region against rapid exchange of sample/analyte (shorter pore length)—depending on the application. The given values are particularly useful for the analysis of body fluids, such as whole blood with an analyte in the plasma fraction of the whole blood sample.

Further, according to some embodiments of the sensor element, the pores are straight. Straight-shaped pores facilitate an effective transport through the length of the pore, thereby achieving a fast sub-sample/analyte exchange.

Further, according to some embodiments of the sensor element, the pores are track-etched pores formed by exposing the translucent membrane to a directional ion bombardment followed by chemical etching. Track etching is particularly well suited for forming straight-shaped and narrow, yet deep pores of e.g. the above-mentioned dimensions. The pores may be formed in a unidirectional arrangement resulting, e.g. from a single directional ion bombardment exposure. Alternatively, the pores may be formed in a multi-directional arrangement by providing multiple directional ion bombardment exposures from different directions. The pore arrangements may thus e.g. be created/defined by one or more directional ion-bombardment exposures prior to performing the etching steps.

A suitable translucent membrane may be produced e.g. from transparent polymer membranes with so-called track-etched pores, similar to those available from the company IT4IP (IT4IP S.A./avenue Jean-Etienne Lenoir 1/1348 Louvain-la-Neuve/Belgium) with the modification that the pores are closed at one end. Through-going pores in the membranes may be closed e.g. by laminating a backing sheet to the backside of the porous membrane, or by decelerating the ions such that the ion-bombardment tracks, and thus the pores etched following these tracks, stop within the transparent polymer membrane to form dead end pores. The membrane is typically backed by a stiff transparent element to provide adequate mechanical strength to the translucent membrane.

The translucent membrane should preferably be made of a material that does not absorb light and at the same time it should be possible to produce the dead end pores in the material e.g. by track etching the material. A material that is suitable for this is, for example, polyethylene terephthalate (PET or PETE) or an analogue of PET (polyethylene terephthalate polyester (PETP or PET-P)) or a polycarbonate (PC). The translucent membrane may comprise a hydrophilic coating of e.g. polyethylene glycol (PEG) to increase the diffusion into the pores. The hydrophilic coating may be chosen so as to configure the sensor element for a certain mode of operation of the sensor element. In some modes of operation, the sensor element will never dry out, once it is in use and it therefore only needs to be hydrophilic at startup. For other modes of operation of the sensor element, a coating is applied that permanently keeps up the hydrophilicity throughout the entire lifetime of the sensor element. This allows for an operation mode where the sensor element is allowed to dry out between subsequent uses, yet maintaining a fast sub-sample extraction from a liquid sample presented at the sensor surface. Consequently, a fast measurement turn-around from contacting the sensor surface with a liquid sample to obtaining an optical probing result can be achieved even though the sensor element is allowed to dry out between uses.

Advantageously according to some embodiments of the sensor element, a porosity of a given volume of the translucent membrane comprising pores, at least within the probing region, is between 50% and 5% by volume, between 30% and 10% by volume, or about 15% by volume. The porosity may be characterized in terms of the volume of the voids created in the translucent membrane by the pores, i.e. the pore volume, wherein the pore volume is referred to the volume of the translucent membrane penetrated by the pores. This volume is here defined as the volume between the front side area over which the pores are distributed and the identical parallel area shifted into the translucent membrane by the maximum depth of penetration of the pores into the translucent membrane as seen in a vertical direction perpendicular to the sensor surface.

In addition thereto, the porosity may be further characterized in terms of the integrated pore volume, which is equal to the sub-sample volume that is available for optical probing. The pore volume may conveniently be expressed as an equivalent pore volume depth DELTA, which is the pore volume referred to the corresponding front side area over which the pore openings are distributed. Accordingly, the porosity of the translucent membrane can be converted into an equivalent pore volume depth DELTA as follows. The pores having an opening within a given front side area A have a total pore volume V. The equivalent pore volume depth is then calculated as the total pore volume divided by the given front side area: DELTA=V/A.

Advantageously according to some embodiments, an equivalent pore volume depth DELTA is less than 20 µm, or less than 15 µm, or less than 10 µm, or in the range from 3 µm to 5 µm, wherein the equivalent pore volume depth DELTA is defined as the total volume of the pores V divided by the front side area A over which the openings of the pores are distributed. Thereby, a small sub-sample with a representative concentration of relevant components is obtained. A small sub-sample volume is desirable to promote a fast sub-sample exchange, thereby reducing response time of the sensor element, and cycle time of measurements using the sensor element. A small sub-sample volume is further desirable in order to avoid effects of depletion of boundary layers of a plasma fraction in a whole blood sample close to the front side of the translucent membrane. Such depletion effect may otherwise occur in small, still standing samples, where e.g. red blood cells may obstruct an efficient diffusive exchange of relevant components from the volume of the whole blood sample towards the boundary layer at the front side of the translucent membrane, if the equivalent pore volume depth exceeds a critical value.

Preferably, an equivalent pore volume depth DELTA is at least 1 µm, alternatively at least 2 µm, or in the range from 3 µm to 5 µm, wherein the equivalent pore volume depth is defined as above. A larger sub-sample volume is desirable to achieve a better signal-to-noise level due to a larger sub-sample volume contributing to the optically probed information on the relevant components in the plasma.

Further according to some embodiments, a useful compromise between reducing response time, reducing cycle time, and/or avoiding depletion effects in small still standing whole blood samples or fluids on the one hand, and a required or desired signal-to-noise ratio on the other hand is found for an equivalent pore volume depth DELTA in the range from 1 µm to 20 µm, preferably in the range from 2 µm to 10 µm or at about 4 µm-5 µm.

Further, according to some embodiments of the sensor element, an inner wall surface of the pores is hydrophilic, e.g. coated with a hydrophilic coating. Thereby, an efficient capillary driven filling of dry pores with liquid is achieved. Furthermore, a hydrophilic coating prevents certain hydrophobic substances, such as hydrophobic dyes, hemoglobin, and other proteins, from depositing inside the pores that would otherwise lead to a gradual fouling of the sensor, which is difficult to wash out with an aqueous solution.

The porous membrane sensor further comprises a reflective layer arranged at the front side of the translucent membrane. The content of the pores can conveniently be probed optically from the back side of the translucent membrane, or more generally, from the side of the reflective layer facing towards the translucent membrane, wherein the reflective layer at the front side optically separates an optical probing region comprising the pores from the fluid contacting the front side of the translucent membrane. The reflective layer is adapted to reflect light reaching the reflective layer from directions from the backside of the translucent membrane, thereby preventing probing light from reaching and interacting with the fluid at the front side of the translucent membrane. The optical probing is thus selectively performed only on the sub-sample inside the pores.

Advantageously, according to some embodiments, the reflective layer is made of metal. Such metallic coatings can be applied in a relatively cost-effective, yet well-controlled manner with adequate reflectivity.

Advantageously, according to some embodiments, the reflective layer is made of platinum, palladium or an alloy comprising as a principal component platinum or palladium. These materials exhibit a good reflectivity in the spectral range of the electromagnetic spectrum (deep violet to blue) that is relevant for the detection of certain substances, e.g. free hemoglobin, for example by absorbance probing. Furthermore, these materials are biocompatible and do not e.g. introduce artificial hemolysis. Furthermore, these materials are chemically stable in general and in particular in the chemical environment of biological fluids, such as a whole blood sample or any of the previously mentioned body fluids.

Alternatively, according to some embodiments, the reflective layer may be made of silver or aluminum. Further advantageously according to some embodiments, the surfaces of the reflective layer facing towards the sample volume are encapsulated by an additional passivation layer, thereby enhancing the lifetime of the device, in particular when using silver or aluminum as a material for the reflective layer. A suitable passivation may be made of e.g. a thin layer of SiO2, which preferably is made transparent and has to be sufficiently thin so as not to obstruct the opening of the pores. These materials may also provide a good reflectivity in the relevant spectral range (red), are biocompatible and chemically stable in the environment.

Advantageously according to some embodiments, the thickness of the reflective layer is between 10 nm-100 nm depending upon the used metal. Such a layer thickness allows for applying the reflective layer by an evaporation technique without clogging of the openings of the pores at the sensor surface. At the same time, the layer thickness has to be sufficient to provide adequate attenuation of light propagating to the sample volume in order to ensure an enhanced optical separation between the probing region and the sample volume containing the fluid to be analyzed, e.g. a whole blood sample. Preferably, the transmitted light is less than 5%, less than 1% or even less than 0.1% in the spectral range of detection, i.e. in the spectral range from which a signal representative of the relevant component is developed. For example, for measuring hemoglobin in the plasma fraction of a whole blood sample suitable spectral ranges are from 380 nm to 700 nm, from 380 nm to 450 nm, from 400 nm to 430 nm, or at about 416 nm.

Advantageously, the sensor surface is planar, thereby facilitating, or at least improving conditions for reliable optical probing.

Advantageously, according to some embodiments, the sample space of the porous membrane sensor element has a cylindrical shape defined by a top wall, a bottom wall opposite to the top wall, and a circumferential wall connecting the top and bottom walls; wherein a feed orifice is arranged at an at an upstream end of the sample space, i.e. as seen in a direction towards the inlet; and wherein a discharge orifice is arranged at a downstream end thereof, i.e. as seen in a direction towards outlet. Preferably, the porous membrane sensor element is arranged in the top wall. According to some embodiments, the cylindrical shape may have a circular cross-section, or an elliptical cross-section as seen in a cut-plane parallel to the sensor surface. Further according to some embodiments, the cylindrical shape may have a polygonal cross-section, as seen in a cut-plane parallel to the sensor surface.

Advantageously, the feed and discharge orifices are arranged in the circumferential wall. Preferably, the feed and discharge orifices are arranged opposite to each other. Thereby, a simple flow pattern for flow through the sample space of the porous membrane sensor element is achieved, when performing fluid handling operations. Consequently, a further smooth and efficient replacement of fluids contacting the sensor surface during fluid handling operations is achieved. Furthermore, cross-contamination may thereby be reduced.

Advantageously, a height of the sample space of the porous membrane sensor element as seen in a direction from the top wall to the bottom wall is less than one half, or less than one third, or less than one fifth, or even less than tenth of a transverse dimension of the sample space of the porous membrane sensor element. Thereby, a smaller volume of the fluid sample is required, without compromising the quality of the measurement performed in the porous membrane sensor element. This feature further benefits from the inventive insight that the measurements in the porous membrane sensor element rely on diffusive exchange of the analyte with a relatively thin border layer of the complex fluid sample contacting the sensor surface, in particular with regard to high molecular weight analytes.

Advantageously, the bottom wall is curved to reduce the distance of the bottom wall from the top wall in a center portion of the sample space of the porous membrane sensor element, as compared to a peripheral portion thereof. Preferably, the porous membrane is arranged in the top wall. Preferably, in this embodiment, the porous membrane is planar. The bottom wall may be curved to bulge at least along a direction from the feed orifice to the discharge orifice towards the top wall, such that the bottom wall is closer to the top wall in a center portion than at the feed/discharge orifices.

Further advantageous embodiments are defined in the following, whereby analogue and further advantages are achieved as disclosed in the present application.

Further, according to some embodiments of the porous membrane sensor element, the input branch and the output branch enclose an acute angle, at least at the coupling interface.

Further, according to some embodiments of the porous membrane sensor element, the input branch and the output branch are straight.

Further, according to some embodiments of the porous membrane sensor element, the input and output branch are arranged in a backscatter configuration.

Further, according to some embodiments of the porous membrane sensor element, the sensor surface is arranged parallel to the axial direction.

Further, according to some embodiments of the sensor assembly, the sensor surface is arranged parallel to the direction of flow from the inlet to the outlet for fluid handling in the sample space of the porous membrane sensor element. Thereby an efficient contacting of the sensor surface with a fluid sample is achieved. Furthermore, a smooth and efficient replacement of fluids contacting the sensor surface during fluid handling operations is achieved. Furthermore, cross-contamination may thereby by reduced.

Further, according to some embodiments of the porous membrane sensor element, the common light guide plane is arranged perpendicular to the axial direction.

Further, according to some embodiments of the porous membrane sensor element, the input branch, the output branch, and the coupling interface are integrally formed in a single piece.

Further, according to some embodiments of the porous membrane sensor element, the light guide core further comprises an inspection port directed towards the coupling interface. As further detailed below, the inspection port is particular useful, e.g. during production of the porous membrane sensor element for proper alignment of a coupling interface of the light guide core with the porous membrane, and/or for inspecting for bubble formation in a padding composition applied between the coupling interface and the porous membrane. The inspection may further be configured as an optical dump for collecting and extracting excessive input light that otherwise might reach the output branch and cause an undesirable background noise. The signal-to-noise ratio for detection of signal from optical interaction with the subsample in the pores is thus able to be enhanced.

Further, according to some embodiments of the porous membrane sensor element, the inspection port is co-planar with the input and output branches. Thereby, the inspection may be configured as a particularly efficient optical dump for collecting and extracting excessive input light that otherwise might reach the output branch and cause an undesirable background noise. The signal-to-noise ratio for detection of signal from optical interaction with the subsample in the pores can thus be enhanced.

Further, according to some embodiments of the porous membrane sensor element, the inspection port is arranged in a forward scattering configuration with respect to the input branch. In this embodiment, the inspection port is configured as a yet further efficient optical dump for collecting and extracting excessive input light that otherwise might reach the output branch and cause an undesirable background noise. Thereby, in particular specular reflections of the input light may be extracted. Consequently, the signal-to-noise ratio for detection of signal from optical interaction with the sub-sample in the pores can thus be enhanced.

Advantageously according to some embodiments, the inspection port may, in particular after assembly of the porous membrane sensor element, be terminated with an absorbing element, such as a blackened end surface, an absorbing surface treatment, or any equivalent optical termination. Thereby, excessive input light may be efficiently removed from the light guide core. Consequently, the signal-to-noise ratio for detection of signal from optical interaction with the subsample in the pores can thus be yet further enhanced.

Further, according to some embodiments of the porous membrane sensor element, the inspection port is integrally formed with the input branch, the output branch, and the coupling interface in a single piece. This embodiment allows for suppressing disturbing optical interference in the light guide core. The signal-to-noise ratio for detection of signal from optical interaction with the subsample in the pores can thus be further enhanced.

Further, according to some embodiments of the porous membrane sensor element, the single piece further comprises a mechanical bridge. The mechanical bridge mechanically connects the input and output branches at distal portions thereof, wherein proximal portions of the input and output branches are pointing towards the coupling interface.

Further, according to some embodiments of the porous membrane sensor element, the optical subassembly further comprises a light guide shell embracing the light guide core. The light guide shell is adapted to provide mechanical support for the light guide, which allows for easy handling, alignment, and/or inspection of the light guide portion during production of the sensor element. Thereby, an enhanced quality of the sensor element production is achieved. Preferably, the light guide shell is configured to optically sheathe the light guide core. Thereby it is achieved to avoid cross-talk from the input branch being shunted directly to the output branch. Preferably, the guide shell is made of a non-transparent material, so as to block any stray light that might emanate from the light guide. The light guide shell thus efficiently suppresses cross-talk between the input and output branches, that would otherwise shunt the desired signal stemming from the probing interaction in the porous membrane sensor. Thereby, the signal to noise ratio can be enhanced significantly.

Advantageously according to some embodiments, the light guide shell is formed as two half shells comprising respective cavities for receiving the light guide core therein. Advantageously, the two half shells are shaped to fully encapsulate the light guide in directions transverse to the direction of guided light propagation. Providing the light guide shell in two half shells thus allows to protect the light guide for easy handling, alignment, and/or inspection of the light guide portion during production of the sensor element. Furthermore, a full encapsulation also provides protection against stray light, thereby improving the signal to noise ratio of the signal probing the porous membrane.

Advantageously according to some embodiments, the light guide shell is formed as a single piece shell, open at the top, wherein a cavity depth is dimensioned to fully receive the light guide therein. Thereby, stray or shunt light may be blocked and/or contained. Consequently, cross-talk from the input branch to the output branch is suppressed. Advantageously, the light guide is embedded in the cavities in a padding material having an optical index within relevant wavelength ranges, which is adapted to ensure light guiding for light travelling along the input and output branches. The padding material may be any suitable composition, such as a transparent UV-curable composition. Relevant wavelength ranges are determined by the wavelength ranges for input and output light for which the sensor element is designed. Providing a single piece shell as a light guide shell has the surprising advantage that the production of the sensor element becomes more precise and reliable as it allows for easy inspection of the quality of filling voids between the light guide and the light guide shell with padding material during and/or after the embedding step. Surprisingly, a good shunt light suppression is nevertheless achieved, in particular when the sensor element is integrated in a sensor assembly with the "open" top of the light guide shell of the sensor element abutting a cooperating wall portion of a sensor port and/or frame structure to which the porous membrane sensor element is attached.

Further, according to some embodiments of the porous membrane sensor element, the light guide shell further comprises engagement means configured to engage corresponding guide means on the porous membrane sensor housing, the engagement and cooperating guide means being adapted to fixing the light guide core with respect to the porous membrane sensor housing. Thereby, an easy assembly of the sensor element is facilitated, wherein at the same time an enhanced precision is achieved for the alignment of the optical subassembly with respect to the porous membrane and the sample chamber in the porous membrane sensor housing.

Advantageously, according to some embodiments of the porous membrane sensor element, the light guide core has vertically projecting distance elements, such as one or more vertically projecting noses, thereby facilitating an easy vertical alignment of the light guide core with respect to the porous membrane, e.g. when mounted in abutment with a cooperating surface of a sensor port and/or frame structure of a sensor assembly.

According to a further aspect, a sensor assembly for analyzing a complex fluid sample comprises a sample chamber extending from an inlet to an outlet, wherein the direction from the inlet to the outlet defines a direction of flow for fluid handling in the sample chamber, wherein the sensor assembly further comprises a porous membrane sensor element according to any of the embodiments disclosed herein; wherein the flow channel of the porous membrane sensor element is integrated in the sample chamber.

Operating the sensor assembly typically includes steps of filling the sample chamber with a fluid by flowing an amount of the fluid from the inlet through the sample chamber to the outlet, stopping the flow when filling is completed, and performing measurements on the fluid sample thus presented in the sample chamber. For example, steps of fluid handling may include steps of rinsing, i.e. flowing a rinsing fluid through the sample chamber in a flow direction from the inlet to the outlet so as to remove any previously presented fluid sample and any contaminants, e.g. stemming from previously presented fluid samples, from the sample chamber. Furthermore, operating a measurement device using the sensor assembly typically includes steps of calibrating the device by means of measurements performed on calibration fluids presented in the sample chamber. Operation of the sample assembly therefore includes frequent fluid handling operations, such as filling, discharging, and refilling of the sample chamber by flowing different fluids through the sample chamber in a direction of flow from the inlet to the outlet.

Advantageously according to some embodiments, the first sample space is a formed as a channel having a top wall, a bottom wall, and sidewalls connecting the top and bottom walls, thereby defining an essentially rectangular cross-section as seen in a cut-plane perpendicular to the principal direction of the first sample space from the inlet to the outlet. Advantageously, the rectangular cross-section of the first sample space has a width as seen in a transverse direction parallel to the top and bottom walls in the range of a few millimeters, such as up to 10 mm, up to 5 mm, or up to 3 mm, and at least 1 mm, or at least 2 mm, such as about 2.4 mm; and a height as seen in a direction perpendicular to the top and bottom walls in the sub-millimeter range, such as less than 1 mm, less than 0.8 mm, less than 0.5 mm, and at least 0.1 mm, or at least 0.2 mm, or at least 0.3 mm, such as about 0.4 mm.

Further, according to some embodiments of the sensor assembly, the flow channel of the porous membrane sensor element is integrated in the sample chamber in a downstream portion thereof, between a first sample space and the outlet.

Further, according to some embodiments of the sensor assembly, the first sample space comprises further sensors for the detection of further analytes in the fluid sample.

Further, according to some embodiments of the sensor assembly, the first sample space comprises one or more further sensor elements for detecting respective further analytes. Thereby, the sensor assembly is adapted for simultaneous analysis with respect to multiple analytes, including both the analyte detectable by the porous membrane sensor element and the further analytes detectable by the one or more further sensor elements arranged in the first sample space.

Further, according to some embodiments, the sensor assembly, or a measurement set-up configured for receiving the sensor assembly, further comprises a light source connected to the optical input port, wherein the light source is configured for emitting probing radiation. Further according to some embodiments, the sensor assembly further comprises a detector connected to the optical output port, wherein the detector is configured for detecting light emerging from the probing region in response to an illumination of the probing region through the input port by the light source, and wherein the detector is adapted to generate a signal representative of the detected light. The light source may be any light source that transmits light in a region where the analyte in the pores absorb light or otherwise provides an optically stimulated response in order for the system to work. Due to their properties with respect to size, weight, efficiency etc. light emitting diodes are preferred for embodiments intended for miniaturization and/or integration in an assembly. The detector may be any optical detection set-up suited for detecting the optical response received from the optical output port, and for analyzing that optical response in order to generate an output signal indicative of the analyte to be detected. Advantageously according to one embodiment, the detector may include a spectrophotometer and an optical probing device is configured for the spectrophotometric analysis of the light emerging from the probing region. This allows for resolving the spectral signature of one or more relevant components in the light emerging from the sub-sample in the probing region. For purposes of miniaturization and compactness, e.g. in the context of point-of-care set-ups, the detector may include a photodiode or a spectrometer that is able to detect the absorption in the entire spectrum. Alternatively, an array or diodes may be used, where each diode emits light at different wavelengths, and a photodiode is used as a detector. The diodes may be multiplexed to emit light in different intervals. The absorption is then found by comparing the light emitted from a diode in that particular interval compared with the light detected by the photodiode.

According to a yet further aspect of the invention, a method of optically detecting an analyte such as hemoglobin in a fluid is provided. The method implements the steps of providing a fluid sample in a sample chamber and optically probing said fluid sample for an analyte, and optional further analytes, as discussed herein in the disclosure of the porous membrane sensor element and the sensor assembly, and at least achieves the same advantages as discussed with respect to the respective embodiments.

According to some embodiments, a method of detecting an analyte in a complex fluid sample comprises the steps of providing a sensor assembly as disclosed above; contacting the sensor surface of the porous membrane sensor element with a reference liquid so as to fill the pores with the reference liquid; contacting the sensor surface with a sample of the complex fluid to be analyzed; waiting for a diffusion time to allow for diffusion of the analyte in the complex fluid into the pores to stabilize; injecting input light into a probing region from a backside of the porous membrane; collecting light emitted from the pores towards the backside of the porous membrane in response to the input light, thereby optically probing the fluid inside the pores; and, based on the result of the optical probing, establishing an analyte level of the complex fluid. Preferably, the reference liquid is an aqueous solution that is compatible with the fluid, and in particular compatible with the fraction thereof that may enter the pores, such as a liquid for rinse, calibration and/or quality control. Advantageously, an analyte is detected optically in the pores by the color change due to the presence of the analyte in representative amounts in the extracted sub-sample. Advantageously according to some embodiments, optical probing comprises performing a spectrophotometric analysis of the light emerging from the pores as an optical response to the probing input light. Advantageously according to some embodiments, optical probing is measuring the absorbance. This has the advantage of a relatively simple, yet effective set-up. In particular, the method comprises steps of fluid handling for contacting the sensor surface of the porous membrane sensor element with the complex fluid sample to be analyzed. When performed using a sensor assembly comprising the porous membrane sensor element integrated in a downstream portion thereof, these steps of fluid handling include flowing the complex fluid to be analyzed through the inlet of the sample chamber, through the first sample space, through a connecting feed channel, the connecting feed channel connecting the first sample space with the second sample space, through the flow channel comprising the sample space of the porous membrane sensor element, and through the outlet, until a predetermined criterion is fulfilled for determining that the sample chamber is filled. The criterion can, e.g. be determined by appropriate fluid interface detectors arranged at the inlet and at the outlet of the sample chamber.

While the present invention has mainly been described herein with reference to uses in the context of the analysis of blood analysis, the skilled person will understand that the present invention is also useful in other context in an equivalent manner without leaving the scope of the present invention.

For example, the sensor element can be used in a reading device for color producing/consuming assays. Such a device has the advantage that it is not necessary to perform separation steps in order to produce plasma before the assay. By way of example, the following types of assays may be performed with a device comprising a sensor element according to embodiments of the invention: sandwich assays, where the receptor ligand could be bound inside the membrane channels; Assays where one part is bound in the pores, e.g. Bromocresol Green Albumin assay, which use Bromocresol Green (BCG), to form a colored complex specifically with albumin. The intensity of the color, measured at 620 nm, is directly proportional to the albumin concentration in the fluid; Enzyme activity assays as e.g. the aspartate aminotransferase (AST) activity assay kit, where the transfer of an amino group from aspartate to α-ketoglutarate results in the generation of glutamate, resulting in the production of a colorimetric (450 nm) product proportional to the AST enzymatic activity present.

The sensor element may also be used in non-medical applications, such as monitoring tasks for beer brewing, wastewater analysis, food testing and in dye production. In beer brewing, a precise color is desired. The sensor element could be used to determine whether or not the beer has the desired color or not by measuring on the liquid and compare the reading with a liquid of correct color. Wastewater could be analyzed for presence or absence of a component. In food testing, liquids such as milk, juices and other slurries, the sensor element could be used for analysis for presence or absence of a constituent or analyte. The sensor element could further be useful in the production of certain chemicals, e.g. in the dye industry, to obtain metrics during the production of a desired color, a desired content or other chemical property of the product.

Advantageously according to some embodiments, the sensor element, or a blood analysis system comprising such a sensor element, further comprises a processor configured for comparing the signal generated by the detector with a predetermined calibration reference to develop a quantitative measure of the analyte level in the fluid. Further, advantageously according to some embodiments, the calibration reference is obtained on a dye-based calibration solution, such as an aqueous solution comprising tartrazine dye. Preferably, the dye-based aqueous solution is prepared from a typical rinse liquid with the addition of the calibration dye, such as tartrazine.

BRIEF DESCRIPTION OF THE DRAWINGS

Preferred embodiments of the invention will be described in more detail in connection with the appended drawings, which show in FIG. 1 an exploded view of a porous membrane sensor element for detecting an analyte in a fluid by optical probing, according to one embodiment.

DETAILED DESCRIPTION

Figure 1:
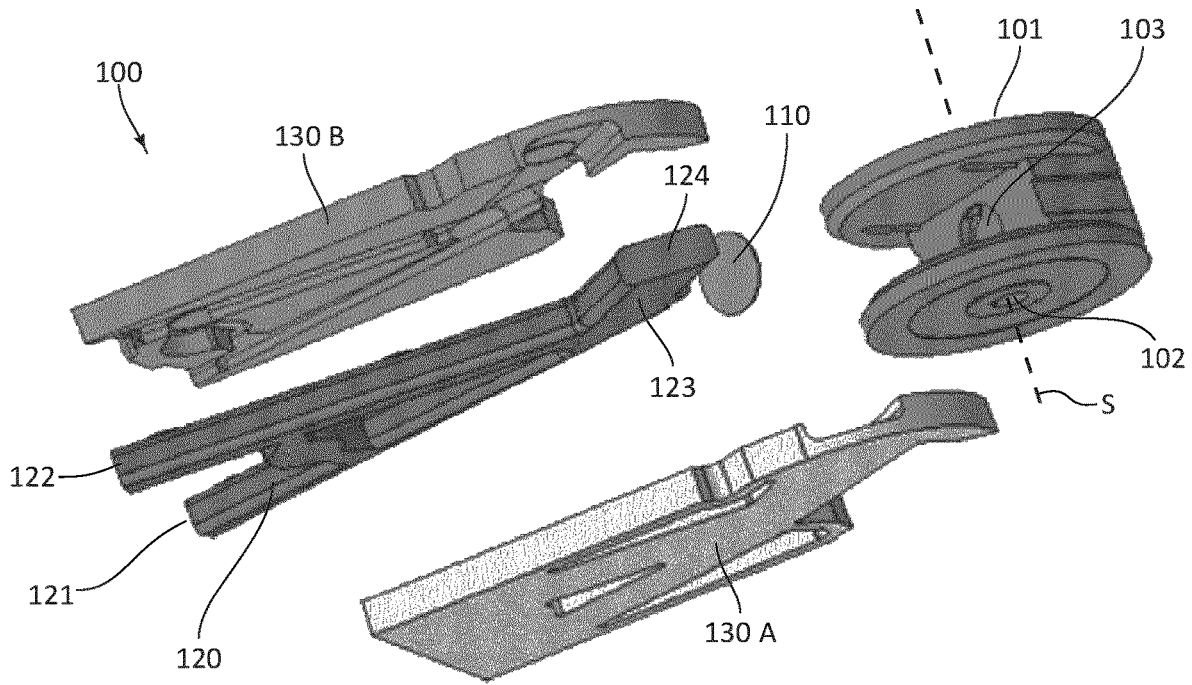

Referring to FIGS. 1-5, a porous membrane sensor element 100 according to one embodiment is now described. FIG. 1 shows an exploded view with components of the porous membrane sensor element 100. The porous membrane sensor element 100 comprises a porous membrane sensor housing 101, which is penetrated by a flow channel 102 defining an axial direction S as indicated by a broken line in FIG. 1. The flow channel 102 comprises a sample space 103 with an opening adapted to receive a planar porous membrane 110 for sealing the sample space 103. The porous membrane 110 is made of a translucent material and has a front side defining a sensor surface facing into the sample space 103 for contacting a fluid sample to be analyzed. Pores are provided extending from the sensor surface into the translucent material as discussed elsewhere herein. Suitable porous membranes are discussed, for example, in the international patent applications by the applicant, WO 2017/085162 A1, WO 2017/085180 A1, and WO 2019/197308 A1, which are hereby incorporated by reference. The sensor surface further comprises a reflective layer, typically made of a metallic material, such as also discussed in these references.

The porous membrane sensor element 100 further comprises an optical probing subassembly with a light guide core component 120. The light guide core component 120 has an input branch 121, and an output branch 122, which are arranged in a common light guide plane, at an acute angle with respect to each other, wherein the input and output branches 121, 122 both are directed towards an optical coupling interface 123. The coupling interface portion 123 is for optical coupling of the optical probing subassembly to the backside of the porous membrane. The light guide core 120 is held in corresponding cavities in a light guide shell of the optical probing subassembly, here seen as two cooperating half shells 130A, 130B. The light guide shell 130A/B is shaped and dimensioned to engage cooperating guide means on the porous membrane sensor housing 101, thereby facilitating an easy assembly and subsequently mechanically supporting and reliably fixing the light guide core 120 to the porous membrane sensor housing 101. In order to improve, during assembly of the porous membrane sensor element, the precision of alignment between the coupling interface 123 and a probing region of the porous membrane 110, in particular with respect to the sample space 103, an inspection port 124 is provided, which gives direct optical access for inspecting said alignment of the coupling interface 123. In a particularly advantageous embodiment, as shown here, the inspection port 124 is arranged co-planar with the input and output branches, and tilted in a forward direction. Thereby, the inspection port also doubles for receiving and extracting so-called shunt light, i.e. light that otherwise might reach the output branch 122. Consequently, the inspection port 124, when configured e.g. as seen here, also contributes to improve the optical signal-to-noise signal.

The light guide core component 120 may further comprise a bridge 125 mechanically connecting distal ends of the input and output branches 121 and 122 with each other. This reduces risks of damaging the fragile branches of the light core component, e.g., when handling the component during assembly. More importantly, the mechanical bridge 125 also acts as a stiffening element, thereby reducing sensitivity of the porous membrane sensor element under operation, e.g. to vibration and/or other mechanical interference.

Figure 2:
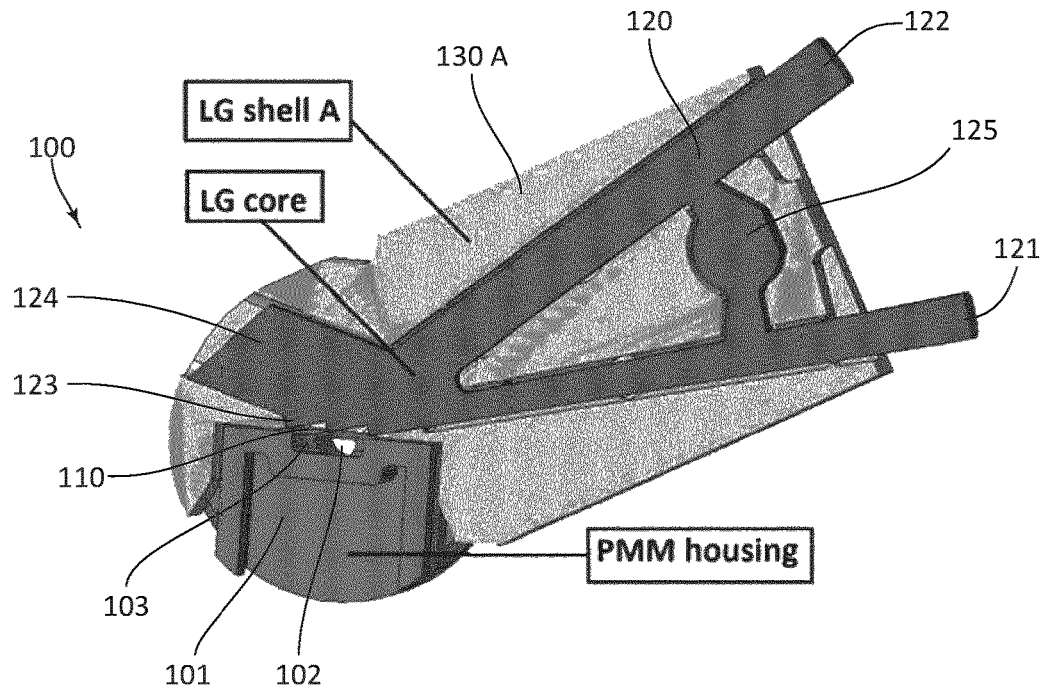
FIG. 2 a cross-sectional view of the porous membrane sensor of FIG. 1, in an assembled state, as seen in a cut-plane perpendicular to an axial direction S.
Figures 3, 4, 5:
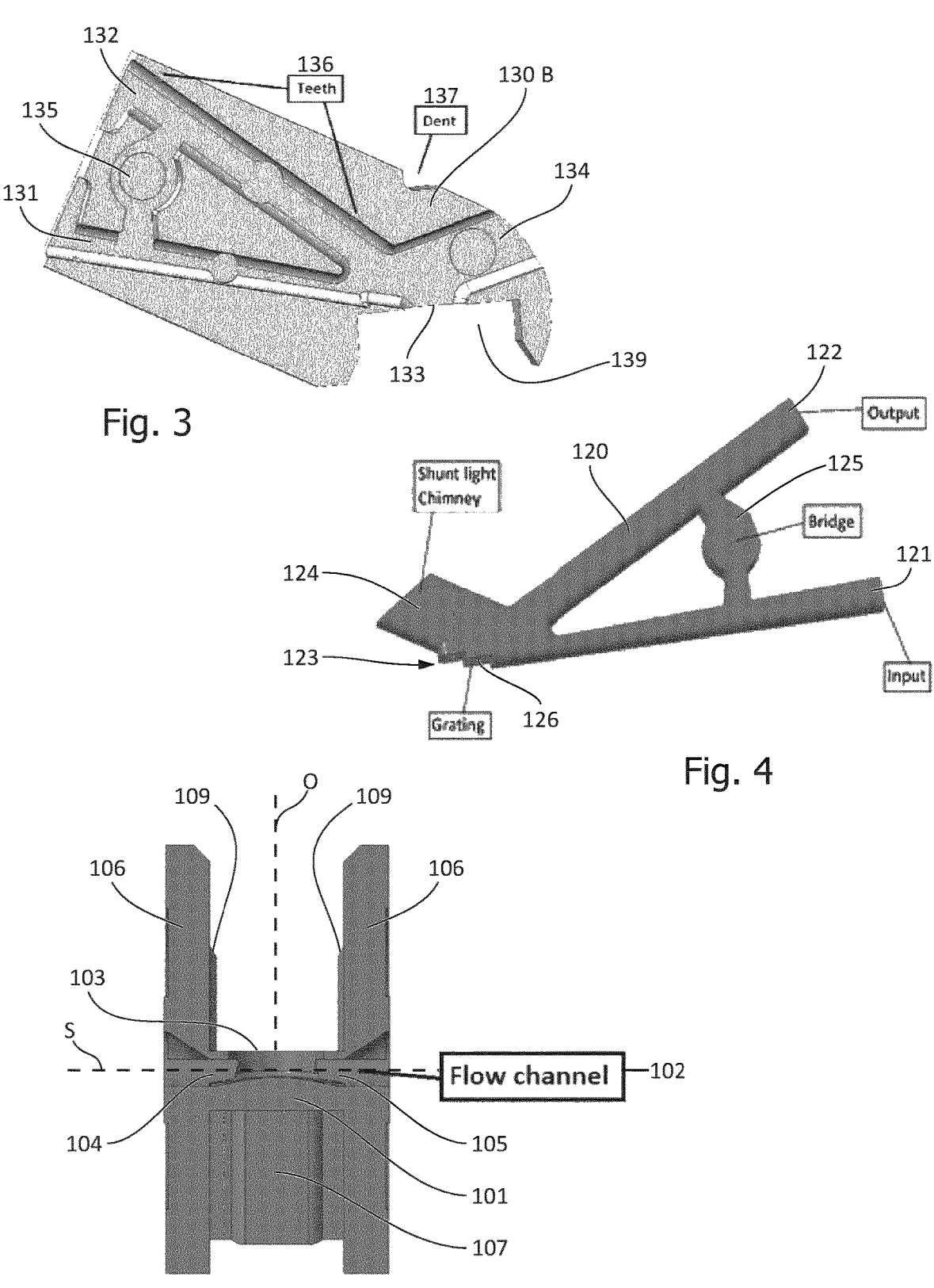
FIG. 3-5 individual components of the porous membrane sensor element of FIG. 1.

FIG. 2 shows a cross-sectional view of the porous sensor element 100 in an assembled state, as seen in a cut-plane essentially perpendicular to the above-mentioned axial direction S as defined by the through going flow channel 102. In particular, FIG. 2 shows the arrangement of the coupling interface 123 with respect to the porous membrane 110 and the sample space 103. The coupling interface 123 contacts the backside of the translucent porous membrane 110 to allow for probing light injected from the input branch 121 to couple into the translucent porous membrane 110, where the probing light can interact with an analyte present in the pores. The coupling interface is further arranged to allow for light emanating from the backside of the translucent porous membrane 110 to be collected by the output branch 122, in particular light that has been scattered by the pores, and thus carries optically probed information about the fluid inside the pores as a signal. The optical subassembly formed by light guide core 120 and the light guide shell 130 is attached to the porous membrane sensor housing 101, wherein side faces and a recess 139 of the light guide shell 130A/B engage cooperating guide means 106, 107, 109 on the porous membrane sensor housing 101. Such further details of the components of the porous membrane sensor element 100 are best seen in FIGS. 3-5 showing a light guide shell 130B, a light guide core 120, and a porous membrane sensor housing 101 (without the porous membrane 110), respectively. Light guide shell 130B has cavities 131, 132, 134, 135 for respectively receiving therein and shaped corresponding to: the input branch 121, the output branch 122, the inspection port 124, and the mechanical bridge 125 of the light guide core 120. An opening 133 arranged in the recess 139 is for receiving the optical coupling interface 123 of the light guide core 120. Alignment features, such as teeth 136 projecting into the cavities allow for maintaining a desired gap between the light guide core and the cavity walls. The gap may be maintained as an air gap. However, the gap is preferably filled by a transparent padding material that may function as a cladding to the light guide core. The light guide shell is preferably made of an absorptive material in order to suppress optical cross talk shunting light from the input branch 121 to the output branch 122 without having interacted with the pores of the porous membrane 110. The optical coupling interface may further comprise one or more steps 126, here also referred to as "Grating". The one or more steps 126 provide an end face oriented essentially perpendicular to the direction of the input branch, and thus leave a wedge shaped gap between the coupling interface 123, and the backside of the porous membrane 110, which is preferably filled with a transparent padding material. The step shaped interface 123, 126 facilitates an improved coupling of input light into the porous membrane 110. As best seen in FIGS. 2 and 4, the particular embodiment shown here has two steps 126 at the optical coupling interface 123.

The input and output branches 121, 122, and in so far applicable the inspection port 124 when configured as a shunt light chimney, are arranged in a common plane of the light guide core 120, which is arranged perpendicular to the sensor surface of the planar porous membrane 110. The plane of the light guide core thus includes the surface normal to the sensor surface as indicated in FIG. 5 by the broken line labelled "O". The input and output branches 121, 122 of the light guide core 120 are arranged in a backscatter configuration, i.e. they are comprised in the same quadrant of the common plane of the light guide core, on the same side of the surface normal O of the porous membrane sensor surface. Thereby artefacts of specular reflections of light originating from the input and reaching the output without interacting with pores in the membrane are effectively suppressed.

Turning now to FIGS. 6-9, a sensor assembly 200 comprising a porous membrane sensor element 100 integrated in an outlet portion thereof is described in the following. Sensor assembly 200 is for use in a fluid sample analyzer device, such as the liquid sample analyzer 1 described further below with reference to FIG. 10. The sensor assembly has a body 201, and inside the body 201 a sample chamber extending from an inlet 210 to an outlet 220. The sample chamber has a first sample space 202 extending from an upstream end in fluid communication with the inlet 210 to a downstream end in fluid communication with the outlet 220. The first sample space comprises at least one, and typically, a plurality of further sensors adapted for detecting respective analytes. The sensor assembly 200 is thus adapted for analyzing a complex fluid sample with respect to multiple analytes, in analogy to, or even compatible with, known sensor assemblies for detecting multiple analytes in a complex fluid sample, such as whole blood samples or other body fluids.

Figure 6:
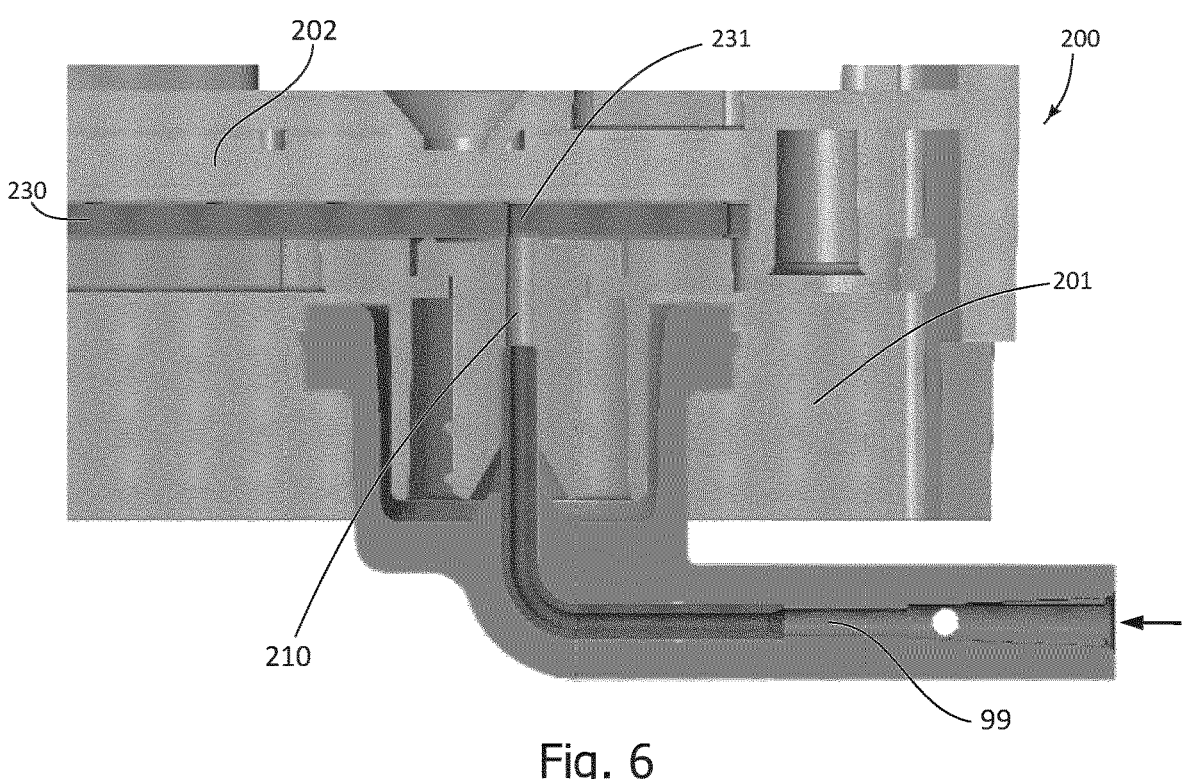
FIG. 6 a cross-sectional detail of an inlet portion of a sensor assembly for the detection of multiple analytes in a fluid sample, according to one embodiment.
Figure 7:
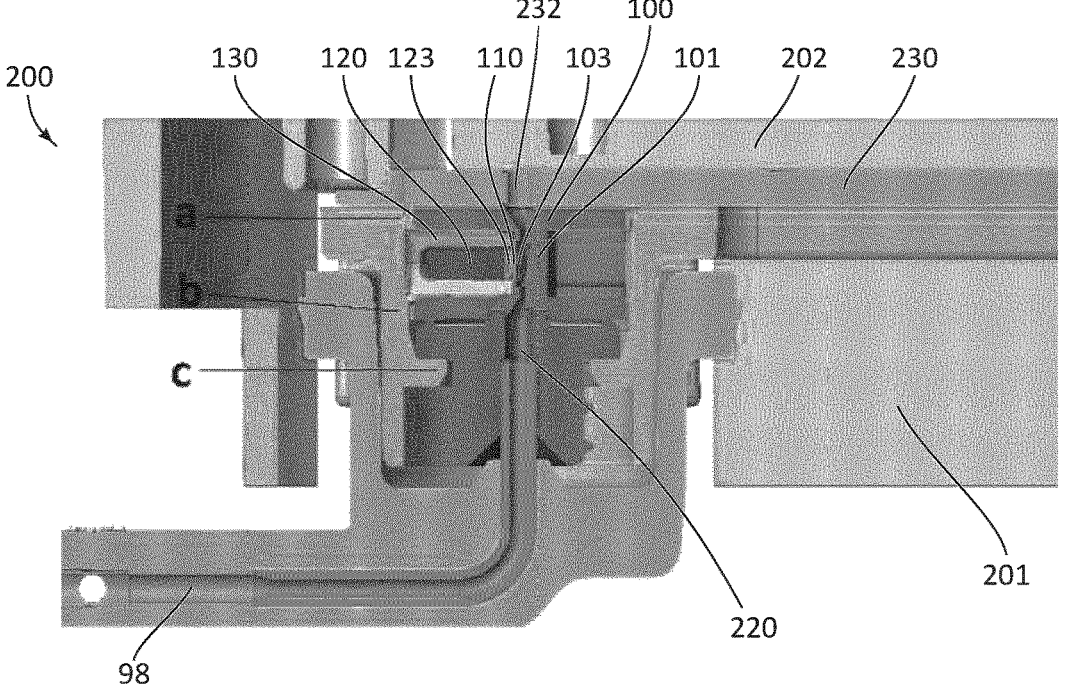
FIG. 7 a cross-sectional detail of an outlet portion of the sensor assembly of FIG. 6, including a porous membrane sensor element.
Figure 8:
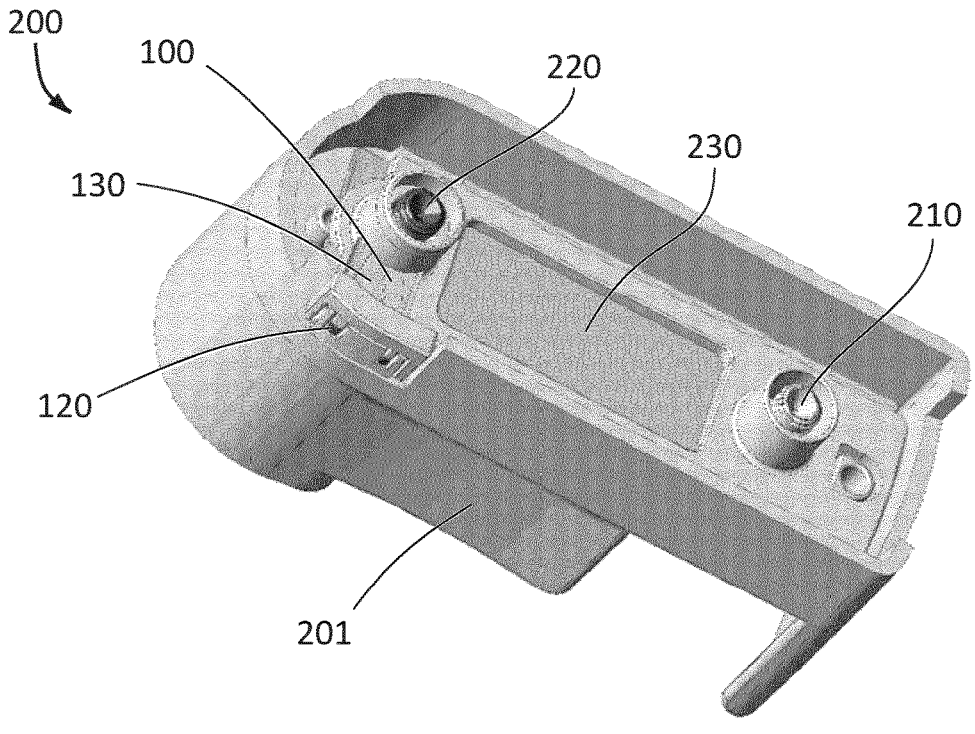
FIG. 8 a perspective view of the sensor assembly of FIG. 6 and FIG. 7 showing inlet and outlet portions thereof, including a porous membrane sensor element.

However, the sensor assembly 200 differs from known sensor assemblies of this type in that the sensor assembly 200 comprises a porous membrane sensor element 100 as disclosed herein. Preferably, as shown in FIGS. 6-8, the porous membrane sensor element 100 is integrated in an outlet portion of the sample chamber, downstream of the first sample space 202, between the first sample chamber 202 and the outlet 220. Nevertheless, it is also conceivable to integrate the porous membrane sensor element 100 as disclosed herein in an analogous manner in an inlet portion of the sample chamber, upstream of the first sample space 202, between the inlet 210 and the first sample space 202.

By the co-planar arrangement of the input and output branches 121, 122 in a backscattering configuration, an intricate, low profile integration is achieved for the porous sensor element 100, which furthermore may be operated for optical probing with input and output arranged at the same side. Due to the flat profile, the porous membrane sensor element 100 may even be integrated such that the sensor assembly 200 is shaped in a manner corresponding to existing sensor assemblies that are not equipped with a porous membrane sensor element, as best seen in FIG. 8. This is, for example, useful for down-compatibility of the sensor assembly 200 with fluid analyzer-devices that do not have an option for optically probing a porous membrane sensor.

Figure 9:
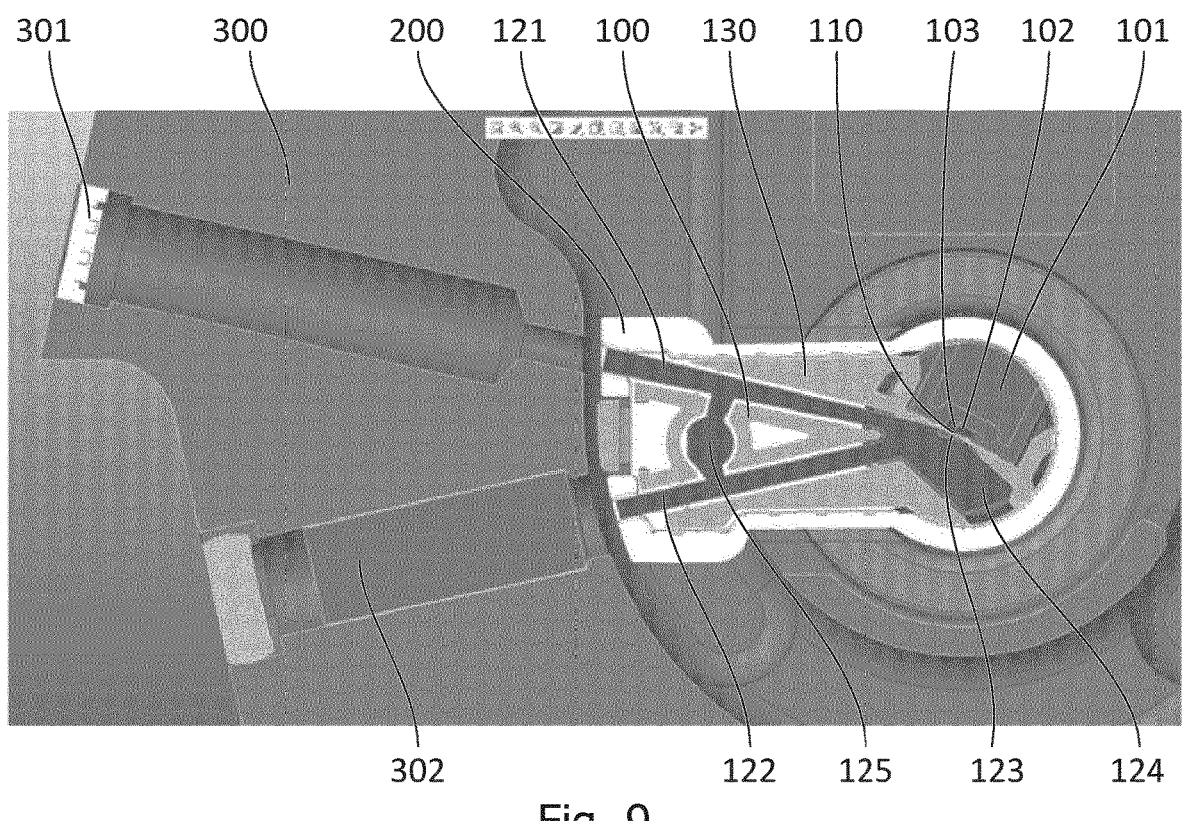
FIG. 9 a cross-sectional detail of a liquid sample analyzer with a sensor assembly as shown in FIG. 8, as seen in a cut-plane perpendicular to an axial direction S of the porous membrane sensor element.

FIG. 9 shows a cross-sectional detail of a liquid sample analyzer port 300 with a sensor assembly 200 as described above, as seen in a cut-plane perpendicular to an axial direction S of the porous membrane sensor element 100. The liquid analyzer port 300 is configured for receiving the sensor assembly 200 for performing fluid handling operations, and for performing optical probing measurements. The analyzer port 300 comprises a light source 301 adapted to inject probing light into the input branch 121. The probing light reaches coupling interface 123 and may interact with an analyte in the pores of the porous membrane 110. The scattered light may be collected through interface 123 by output branch 122, and transmitted to an optical detector 302. The optical detector 302 may then produce a detector signal indicative of the analyte in the pores of the porous membrane 110, and thus of the analyte in a complex fluid sample in the sample space 103.

Figure 10:
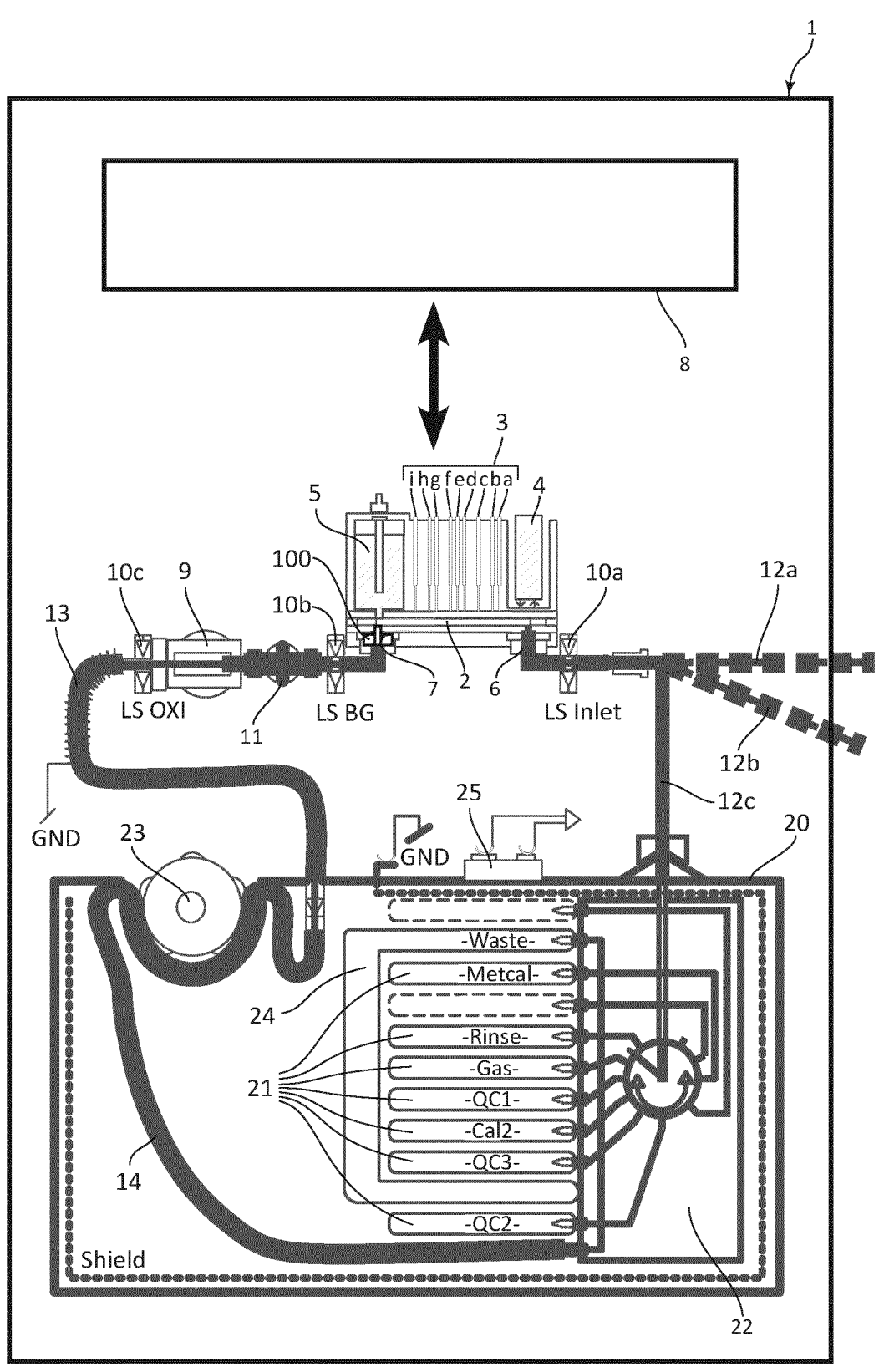
FIG. 10 a diagram of a liquid sample analyzer according to one embodiment.

FIG. 10 shows schematically a liquid sample analyzer 1 with an analyzer part having a signal processor 8, one or more analyte sensors 3(a-i), 4, a measurement chamber 2, and fluid handling infrastructure 20. For performing measurements, the user may provide a liquid sample at an input port 12a/b of the analyzer 1. The liquid sample is transferred through an inlet port 6 to the first sample space 2 of the sample chamber, the first sample space 2 comprising a plurality of analyte sensors 3, 4. The analyte sensors 3, 4 are arranged to provide essentially simultaneous measurements on analyte parameters in a complex liquid sample, e.g. a whole blood sample. Preferably, the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 1. Following pre-programmed instructions loaded in a signal processor 8 and/or user input, measurements are performed using the analyte sensors 3, 4. The analyte sensors 3, 4 generate signals that are representative of a physical parameter for the respective analyte and provide the signals to the signal processor 8 of the analyzer part. The signal processor 8 is adapted to receive and process signals from the analyte sensors 3, 4, and present the processed signals as output to a user or to a subsequent/further data analysis. After measurement, the liquid sample is discharged, and the sample chamber is prepared for the next measurement.

The embodiment of the analyzer shown in FIG. 10 is particularly adapted for the measurement of blood parameters, and further comprises an optional oxygenation measurement device 9 downstream of the sample assembly. Performing the measurements, calibration tasks, and quality control procedures thus typically involves the loading, unloading, rinsing, cleaning and re-loading of different liquids, which may be done by the fluid handling infrastructure 20. The fluid handling may be controlled in an automated way by the signal processor 8 according to pre-programmed instructions and/or user input. The fluid handling infrastructure 20 includes a number of reservoirs 21 pre-filled with process liquids (RINSE/CAL1, CAL2, QC1, QC2, QC3) for rinsing/wash-out, calibration and quality control tasks. The process liquids (RINSE/CAL1, CAL2, QC1, QC2, QC3) have a known composition. The exact composition of a given batch may be stored in a chip 25 that may be attached to a cassette comprising the reservoirs 21, wherein the chip 25 may be read by the signal processor 8. The process liquid (RINSE/CAL1, CAL2, QC1, QC2, QC3) for a given process step may be selected by a fluid selector valve 22, and via feed line 12c transferred through the inlet port 6 to the sample chamber. Correct filling of the sample chamber may be monitored and verified by visual inspection or according to known procedures by observing the propagation of a liquid interface through the system by means of liquid sensors 10a, 10b, 10c located upstream and downstream of the sample chamber, such as at the inlet 6 ("LS inlet" 10a), at the outlet 7 ("LS BG" 10b), and just after the oxygenation measurement device 9 ("LS OXI" 10c), respectively. The fluid flow through the analyzer is driven by a pump 23, here a peristaltic hose-pump arranged downstream of the sample chamber and the oxygenation measurement device 9 and connected thereto via fluid line 13. The discharged fluids are finally transported through fluid line 14 to the waste reservoir 24.

Upon start-up and, in an ongoing manner, during uptime, the analyzer 1 performs self-control routines. If any abnormality is detected, the analyzer 1 indicates the deviation to a user, and may further indicate ways of overcoming an error state. On the other hand, when the analyzer indicates normal operation, measurements can be performed immediately. Advantageously according to some embodiments, the self-control routines may be performed during idle times, i.e. when the analyzer is in an idle state, where it is not used for performing actual measurements on a user's sample. The self-control routines may include continued repetitive measurements performed on a calibration-grade process liquid with a precisely known composition, as e.g. stored on chip 25. The signals obtained for each of the different analyte sensors 3, 4 on the well-known composition may then be used to update continuously the reference for the respective analyte measurements.

The porous membrane sensor element 100 with a second sample space 102 is integrated in the downstream portion of the sample chamber, between the first sample space 2 and the outlet 7. The second sample space is connected to the first sample space through a short feed channel as discussed above with respect to FIG. 7.

Figure 11:
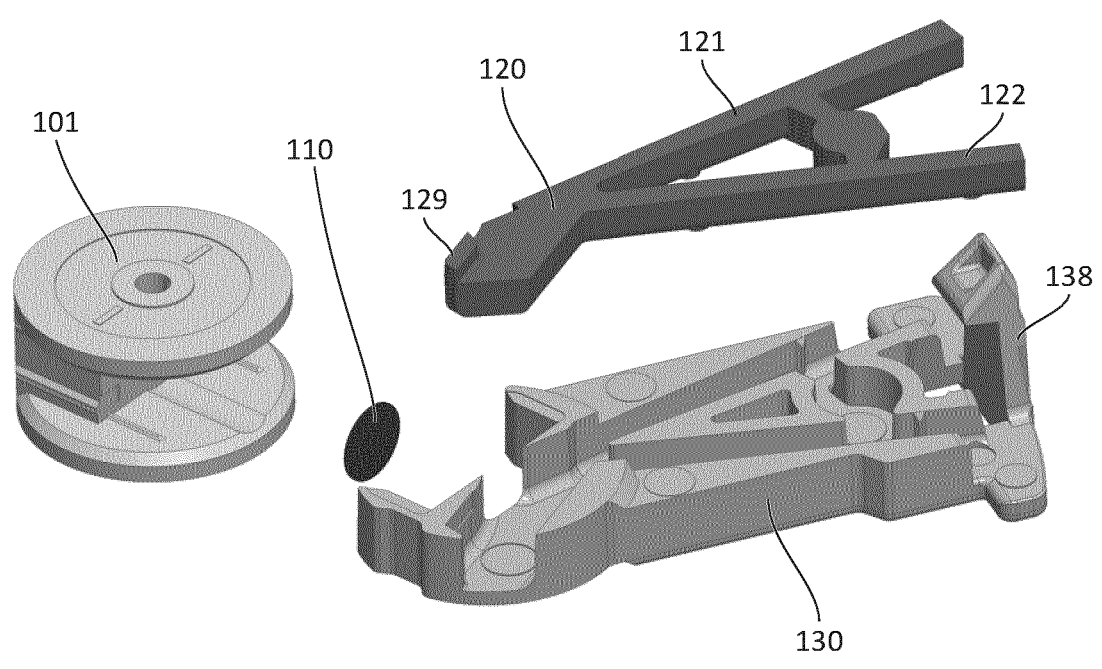
FIG. 11 an exploded view of a porous membrane sensor element for detecting an analyte in a fluid by optical probing, according to a further embodiment; and in FIG. 12 an exploded view of the porous membrane sensor element of FIG. 11, together with a cooperating frame structure portion of a sensor assembly showing inlet and outlet portions thereof.
Figure 12:
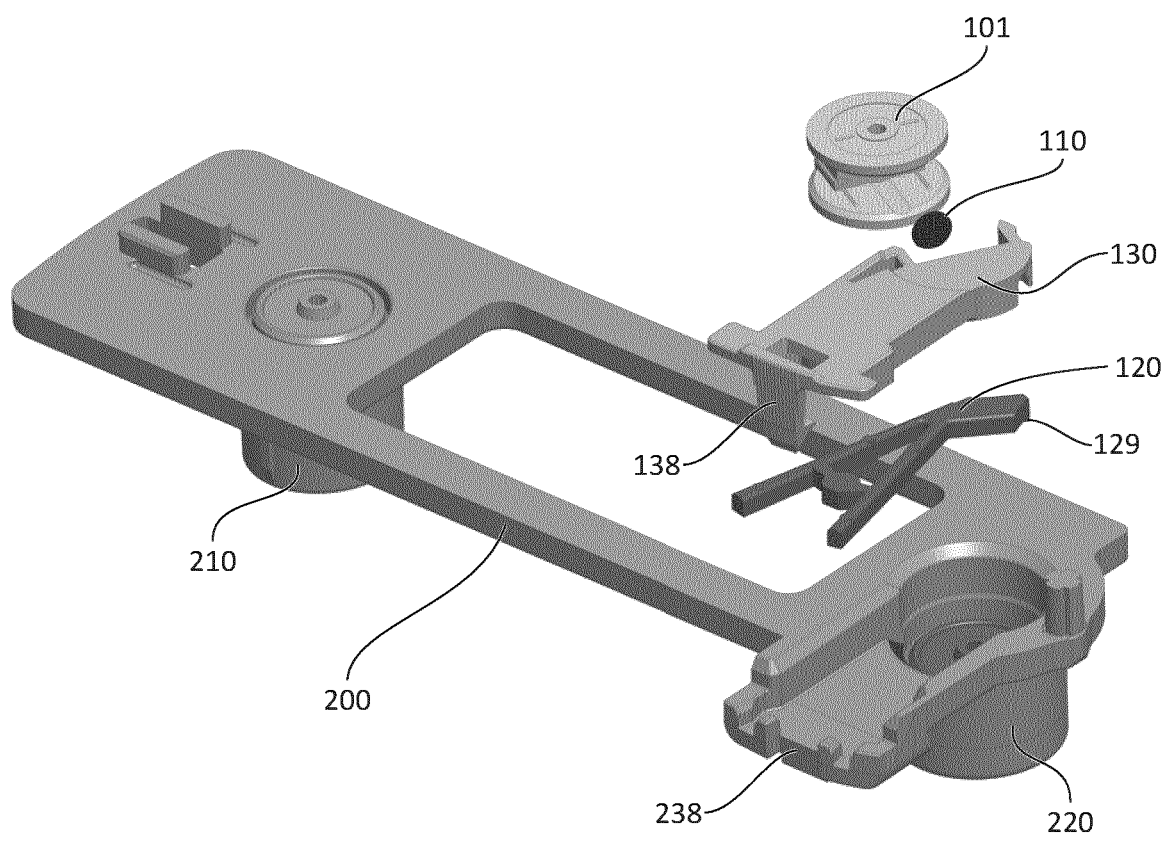

Referring to FIGS. 11 and 12, a porous membrane sensor element 100 according to a further embodiment is now described. FIG. 11 shows an exploded view with components of the porous membrane sensor element 100. FIG. 12 shows an exploded view of the porous membrane sensor element of FIG. 11 upside down, together with a cooperating frame structure portion of a sensor assembly 200 having inlet and outlet portions 210, 220. The porous membrane sensor element 100 comprises a porous membrane sensor housing 101, and a planar porous membrane 110 as already described above with reference to FIGS. 1-5.

The porous membrane sensor element 100 further comprises an optical probing subassembly with a light guide core component 120 as also described above, with reference to FIGS. 1-5. Also the light guide core 120 is held in corresponding cavities in a light guide shell 130 of the optical probing subassembly. However, instead of the two cooperating half shells 130A, 130B shown in the embodiment of FIGS. 1-5, the light guide shell 130 of the embodiment shown in FIGS. 11 and 12 is formed as a single piece shell, which is open at a top side thereof. The depth of the cavities of the light guide shell 130 of FIGS. 11-12 is dimensioned to fully receive the light guide core therein. Thereby, stray or shunt light may be blocked and/or contained. Consequently, cross-talk from the input branch to the output branch is suppressed. The light guide shell 130 is also here shaped and dimensioned to engage cooperating guide means on the porous membrane sensor housing 101 as described above with reference to FIGS. 1-5, thereby facilitating an easy assembly and subsequently mechanically supporting and reliably fixing the light guide core 120 to the porous membrane sensor housing 101.

Alignment features, such as teeth projecting into the cavities allow for maintaining a desired gap between the light guide core and the cavity walls. The gap may be maintained as an air gap. However, the gap is preferably filled by a transparent padding material that may function as a cladding to the light guide core. Advantageously, the light guide core is fully embedded in a padding material. By way of example, the padding may be a UV-curable composition. Further advantageously, the light guide core 120 has vertically projecting distance elements, such as vertically projecting nose 129, facilitating an easy vertical alignment of the light guide core with respect to the porous membrane, when mounted in abutment with a cooperating surface of a sensor port and/or frame structure of a sensor assembly 200 as shown in FIG. 12. The light guide shell is preferably made of an absorptive material in order to suppress optical cross talk shunting light from the input branch 121 to the output branch 122 without having interacted with the pores of the porous membrane 110. Further advantageously, the light guide shell 130 may comprise snap fit engagement means, such as snap fit clamp 138, thereby facilitating a precise, reliable, and easy attachment to a cooperating flange 238 on a frame structure of the sensor assembly 200, as best seen in FIG. 12.

The invention claimed is:

1. A porous membrane sensor element for a detection of an analyte in a complex fluid sample, the porous membrane sensor element comprising:
   (a) a porous membrane sensor housing defining a flow channel defining an axial direction, the flow channel comprising a sample space;
   (b) a porous membrane with a front side defining a sensor surface for contacting the fluid sample, the sensor surface facing towards the sample space, the porous membrane comprising pores extending from respective openings at the sensor surface into the porous membrane, wherein the pores are configured to diffuse the analyte of the complex fluid sample from the sample space; and
   (c) an optical subassembly comprising a light guide, the light guide comprising:
      (i) an input branch,
      (ii) an output branch, and
      (iii) a coupling interface;

wherein the light guide is arranged to contact a back-side of the porous membrane opposite to the front side and facing away from the sample space;

wherein the input and output branches are directed towards the coupling interface;

wherein the input branch and the output branch are positioned closer to the backside than to the front side and are discrete from one another;

wherein the input branch and the output branch are arranged in a common light guide plane arranged perpendicular to the sensor surface.

2. The porous membrane sensor element according to claim 1, wherein the input branch and the output branch enclose an acute angle, at least at the coupling interface.

3. The porous membrane sensor element according to claim 1, wherein the input branch and the output branch are straight.

4. The porous membrane sensor element according to claim 1, wherein the input and output branch are arranged in a backscatter configuration.

5. The porous membrane sensor element according to claim 1, wherein the sensor surface is arranged parallel to the axial direction.

6. The porous membrane sensor element according to claim 1, wherein the common light guide plane is arranged perpendicular to the axial direction.

7. The porous membrane sensor element according to claim 1, wherein the input branch, the output branch, and the coupling interface are integrally formed in a single piece.

8. The porous membrane sensor element according to claim 1, wherein the light guide further comprises an inspection port directed towards the coupling interface.

9. The porous membrane sensor element according to claim 8, wherein the inspection port is co-planar with the input and output branches.

10. The porous membrane sensor element according to claim 8, wherein the inspection port is arranged in a forward scattering configuration with respect to the input branch.

11. The porous membrane sensor element according to claim 8, wherein the inspection port is integrally formed with the input branch, the output branch, and the coupling interface in a single piece.

12. The porous membrane sensor element according to claim 7, wherein the single piece further comprises a mechanical bridge.

13. The porous membrane sensor element according to claim 1, wherein the optical subassembly further comprises a light guide shell embracing the light guide.

14. The porous membrane sensor element according to claim 13, wherein the light guide shell further comprises engagement means configured to engage corresponding guide means on the porous membrane sensor housing, the engagement and cooperating guide means being adapted to fixing the light guide with respect to the porous membrane sensor housing.

15. The porous membrane sensor element according to claim 9, wherein the inspection port is arranged in a forward scattering configuration with respect to the input branch.

16. The porous membrane sensor element according to claim 9, wherein the inspection port is integrally formed with the input branch, the output branch, and the coupling interface in a single piece.

17. The porous membrane sensor element according to claim 11, wherein the single piece further comprises a mechanical bridge.

* * * * *